United States Patent
Liu et al.

(10) Patent No.: US 10,987,431 B2
(45) Date of Patent: Apr. 27, 2021

(54) PREPARATION METHOD OF ADIPOSOMES, AND USE THEREOF

(71) Applicant: Institute Of Biophysics, Chinese Academy Of Sciences, Beijing (CN)

(72) Inventors: Pingsheng Liu, Beijing (CN); Yang Wang, Beijing (CN); Xiaoming Zhou, Beijing (CN); Xuejing Ma, Beijing (CN); Chang Zhou, Beijing (CN)

(73) Assignee: INSTITUTE OF BIOPHYSICS, CHINESE ACADEMY OF SCIENCES, Beijing (CN)

(*) Notice: Subject to any disclaimer, the term of this patent is extended or adjusted under 35 U.S.C. 154(b) by 8 days.

(21) Appl. No.: 16/065,659

(22) PCT Filed: Nov. 22, 2016

(86) PCT No.: PCT/CN2016/106732
§ 371 (c)(1),
(2) Date: Jun. 22, 2018

(87) PCT Pub. No.: WO2017/107728
PCT Pub. Date: Jun. 29, 2017

(65) Prior Publication Data
US 2019/0254972 A1 Aug. 22, 2019

(30) Foreign Application Priority Data
Dec. 23, 2015 (CN) .......................... 201510974956.6

(51) Int. Cl.
*A61K 9/127* (2006.01)
*A61K 31/47* (2006.01)
(Continued)

(52) U.S. Cl.
CPC .......... *A61K 47/6911* (2017.08); *A61K 9/127* (2013.01); *A61K 47/14* (2013.01);
(Continued)

(58) Field of Classification Search
None
See application file for complete search history.

(56) References Cited

U.S. PATENT DOCUMENTS

| 5,651,991 A | 7/1997 | Sugiyama et al. |
| 6,413,942 B1 * | 7/2002 | Felgner ............... A61K 9/1272 514/44 R |

(Continued)

FOREIGN PATENT DOCUMENTS

| CN | 1042080 A | 5/1990 |
| CN | 1717223 A | 1/2006 |

(Continued)

OTHER PUBLICATIONS

Straub et al. Adipophilin/perilipin-2 as a lipid droplet-specific marker for metabolically active cells and diseases associated with metabolic dysregulation (Histopathology, 2013, 62:617-6312). (Year: 2013).*

Ferezou et al. Structure and Metabolic Fate of Triacylglycerol- and Phospholipid-Rich Particles of Commercial Parenteral Fat Emulsions (Nutr Clin Met, 1998, 12:89-97) (Year: 1998).*

(Continued)

*Primary Examiner* — Arthur S Leonard
(74) *Attorney, Agent, or Firm* — McCoy Russell LLP

(57) ABSTRACT

A preparation method of adiposomes, and use thereof. Provided is a method for preparing adiposomes consisting of neutral lipids and a monolayer phospholipid membrane, comprising a1) vortexing phospholipid and neutral lipids in a buffer, centrifuging the resulting mixture, and collecting an upper liquid phase; a2) purifying the upper liquid phase twice or more by uniformly mixing the upper liquid phase with the buffer, layering the mixture, and collecting an upper liquid phase; and a3) uniformly mixing the upper liquid phase obtained in step a2) with the buffer, layering the mixture, and collecting a lower liquid phase in containing adiposomes. For the adiposomes prepared by the method, one or more resident proteins and/or functional proteins can be recruited to obtain artificial lipid droplets, and one or (Continued)

more apolipoproteins can be recruited to obtain artificial lipoproteins; and they all play important roles in preparing drugs and/or drug carriers.

16 Claims, 11 Drawing Sheets
Specification includes a Sequence Listing.

(51) Int. Cl.
- A61K 47/69 (2017.01)
- A61K 47/42 (2017.01)
- C07K 14/47 (2006.01)
- A61K 47/14 (2017.01)
- A61K 47/24 (2006.01)

(52) U.S. Cl.
CPC .............. A61K 47/24 (2013.01); A61K 47/42 (2013.01); C07K 14/47 (2013.01)

(56) References Cited

U.S. PATENT DOCUMENTS

| | | | |
|---|---|---|---|
| 6,586,409 B1* | 7/2003 | Wheeler | A61K 9/1272 514/44 R |
| 2002/0041895 A1* | 4/2002 | Gregoriadis | A61K 9/127 424/450 |
| 2002/0051813 A1* | 5/2002 | Boni | A61K 9/1277 424/450 |
| 2004/0204354 A1 | 10/2004 | Nelson et al. | |
| 2005/0282237 A1* | 12/2005 | Ishimori | G01N 33/5432 435/7.92 |
| 2009/0081284 A1* | 3/2009 | Kojima | A61K 9/0019 424/450 |
| 2009/0226887 A1* | 9/2009 | Brisson | G01N 33/5432 435/5 |
| 2014/0234404 A1* | 8/2014 | Mansour | A61K 39/39 424/450 |

FOREIGN PATENT DOCUMENTS

| | | |
|---|---|---|
| CN | 1870894 A | 11/2006 |
| CN | 1897918 A | 1/2007 |
| CN | 105483076 A | 4/2016 |
| WO | 2005048952 A2 | 6/2005 |
| WO | 2011127456 A2 | 10/2011 |
| ZA | 200602248 B | 9/2007 |

OTHER PUBLICATIONS

Arisawa et al., Saturated fatty acid in the phospholipid monolayer contributes to the formation of large lipid droplets. Biochemical and Biophysical Research Communications 480 (2016) 641-647 (Year: 2016).*

Niakatogawa, H. et al., "Atg8, a Ubiquitin-like Protein Required for Autophagosome Formation, Mediates Membrane Tethering and Hemifusion," Cell, vol. 130, No. 1, Jul. 13, 2007, 14 pages.

Krahmer, N. et al., "Phosphatidylcholine Synthesis for Lipid Droplet Expansion Is Mediated by Localized Activation pf CTP:Phosphocholine Cytidylyltransferase," Cell Metabolism, vol. 14, No. 4, Oct. 5, 2011, 12 pages.

Ding, Y. et al., "Isolating lipid droplets from multiple species," Nature Protocols, vol. 8, No. 1, Jan. 2013, Published Online Dec. 6, 2012, 9 pages.

Yu, J. et al., "Lipid droplet remodeling and interaction with mitochondria in mouse brown adipose tissue during cold treatment," Biochimicia et Biophysica Acta, vol. 1853, No. 5, May 2015, Published Online Feb. 2, 2015, 11 pages.

ISA State Intellectual Property Office of the People's Republic of China, International Search Report Issued in Application No. PCT/CN2016/106732, dated Feb. 3, 2017, WIPO, 11 pages.

Peitsch, M. et al., "A Purification Method for Apolipoprotein A-I and A-II," Analytical Biochemistry, vol. 178, No. 2, May 1989, 5 pages.

Hu, W. et al., "Resonance assignments for the substrate binding domain of Hsp70 chaperone Ssa1 from *Saccharomyces cerevisiae*," Biomolecular NMR Assignments, vol. 9, No. 2, Oct. 2015, Published Online Feb. 15, 2015, 4 pages.

Wang, X. et al., "Research overviews of multivesicular liposomes," Chinese Journal of New Drugs, vol. 15, No. 15, Dec. 31, 2006, 5 pages. (Submitted with English Abstract).

Krahmer, N. et al., "Phosphatidylcholine Synthesis for Lipid Droplet Expansion Is Mediated by Localized Activation of CTP:Phosphocholine Cytidylyltransferase," Cell Metabolism, vol. 14, No. 4, Oct. 5, 2011, 26 pages.

Ding, Y. et al., "Identification of the major functional proteins of prokaryotic lipid droplets," Journal of Lipid Research, vol. 53, No. 3, Mar. 2012, Available Online Dec. 15, 2011, 13 pages.

Liu, P. et al., "Reconstruction of Adiposome and Artificial Lipid Droplets," The FASEB Journal, vol. 29, No. 1—Supplement, Apr. 1, 2015, 2 pages.

Wang, Y. et al., "Construction of Nanodroplet/Adiposome and Artificial Lipid Droplets," ACS Nano, vol. 10, No. 3, Mar. 22, 2016, Published Online Mar. 1, 2016, 11 pages.

* cited by examiner

SEQUENCE LISTING

```
<160> NUMBER OF SEQ ID NOS: 14

<210> SEQ ID NO 1
<211> LENGTH: 831
<212> TYPE: DNA
<213> ORGANISM: Artificial Sequence
<220> FEATURE:
<223> OTHER INFORMATION: MLDS gene

<400> SEQUENCE: 1
atgactgacc agaagaccat cgacagcgtc aagacctcgc tgtacgcggc cgtaggcgcc     60
ggagacgtcg tcgtgcaggc cgtggccgac gtcgtcgccc aggtccgctc gcgcgccgag    120
tccacccagg gtgacgtcga agagcgtgtc ggcggcgcca aggagcgcat cgccggactc    180
caggaagagg tcaccgaggg tgtcgagaac cttcgcgacc gcctcgccgg actgccgtcc    240
gagctgcccg aggagcttgc cgagctgcgt gagaagttca ccgccgacga gctgcgcaag    300
gttgccgagg cctacctgaa ggtcgcctcc gacctgtaca cgtcgctcgc cgagcgcggc    360
gaggacaccg tcgagcgcat ccgcaagcag ccggtcgtcg aggagggcat cggccgcgcc    420
gagaccgcct tcggtgacgc cgtcgagctg accgaggaag ctctcggcac cgttgcacgc    480
cagacgcgcg ccgtcggcga gcaggccgca aagctcgcgg gccgcgcttc gggtcgcatc    540
tccgacaccg ccgagggact cggcgaggcc atcgccgacg ccggcgacga ggctgccctg    600
aaggttctcg acctgggcga ccaggccgag gaagcgtcga aggacgctgc cgatcgcgtc    660
accgccaccg cggccgacgt ccaggctcgc gccgacaagg ctgccccggc caagcacgcc    720
gctcccgcga agaaggctgc tccggccaag gctgcggcaa ccccggcccc ggccccggcc    780
aagaaggccg ccgctccggc caagaaggct gctccggcca agaaggcttg a             831

<210> SEQ ID NO 2
<211> LENGTH: 276
<212> TYPE: PRT
<213> ORGANISM: Artificial Sequence
<220> FEATURE:
<223> OTHER INFORMATION: MLDS protein

<400> SEQUENCE: 2

Met Thr Asp Gln Lys Thr Ile Asp Ser Val Lys Thr Ser Leu Tyr Ala
1               5                   10                  15

Ala Val Gly Ala Gly Asp Val Val Val Gln Ala Val Ala Asp Val Val
                20                  25                  30

Ala Gln Val Arg Ser Arg Ala Glu Ser Thr Gln Gly Asp Val Glu Glu
            35                  40                  45

Arg Val Gly Gly Ala Lys Glu Arg Ile Ala Gly Leu Gln Glu Glu Val
        50                  55                  60

Thr Glu Gly Val Glu Asn Leu Arg Asp Arg Leu Ala Gly Leu Pro Ser
65                  70                  75                  80

Glu Leu Pro Glu Glu Leu Ala Glu Leu Arg Glu Lys Phe Thr Ala Asp
                85                  90                  95
```

Glu Leu Arg Lys Val Ala Glu Ala Tyr Leu Lys Val Ala Ser Asp Leu
             100                 105                 110

Tyr Thr Ser Leu Ala Glu Arg Gly Glu Asp Thr Val Glu Arg Ile Arg
         115                 120                 125

Lys Gln Pro Val Val Glu Glu Gly Ile Gly Arg Ala Glu Thr Ala Phe
     130                 135                 140

Gly Asp Ala Val Glu Leu Thr Glu Gly Ala Leu Gly Thr Val Ala Arg
145                 150                 155                 160

Gln Thr Arg Ala Val Gly Gln Ala Ala Lys Leu Ala Gly Arg Ala
                 165                 170                 175

Ser Gly Arg Ile Ser Asp Thr Ala Glu Gly Leu Gly Glu Ala Ile Ala
             180                 185                 190

Asp Ala Gly Asp Glu Ala Ala Leu Lys Val Leu Asp Leu Gly Asp Gln
         195                 200                 205

Ala Glu Glu Ala Ser Lys Asp Ala Ala Asp Arg Val Thr Ala Thr Ala
     210                 215                 220

Ala Asp Val Gln Ala Arg Ala Asp Lys Ala Ala Pro Ala Lys His Ala
225                 230                 235                 240

Ala Pro Ala Lys Lys Ala Ala Pro Ala Lys Ala Ala Thr Pro Ala
                 245                 250                 255

Pro Ala Pro Ala Lys Lys Ala Ala Ala Pro Ala Lys Lys Ala Ala Pro
             260                 265                 270

Ala Lys Lys Ala
             275

<210> SEQ ID NO 3
<211> LENGTH: 1257
<212> TYPE: DNA
<213> ORGANISM: Artificial Sequence
<220> FEATURE:
<223> OTHER INFORMATION: MDT-28 gene

<400> SEQUENCE: 3

```
atgactgacg tcgagcagcc agtatcagtt gaggatcaac aagcccaagc ccaaagctac     60
tacgatcaag tcttaggaaa tgcttacgta caaacggcaa tcaatgcata cacaaagact    120
aaagagttcc atccacttct taactccaca ttgaattcag ccgaagaaaa ggtttccact    180
gtcggaaatt atgcggctca aaaagccctat gacggataca attcgtacta cgttaagcca    240
aagaacaccg cttatgaagc agtctcttat ggaaccgaga gggccaaaac agctgttgag    300
agcggaaagc aagctgctat cgttggtggt acattcggaa ttggagctgc cgtcgttttg    360
acccaattct cacttgcctt gagtgctgga ggtgccgccc tggtccttga gcaagtggac    420
agtgctaaaa agttgggaag cagcgcgatt tctacgatca agaagccga gcttgctgtc    480 gaacacagaa tcttctcagc tcttcatcag gcccaacgaa tcgccatggt tcctgtggag    540
aaaatcacag aaaatactaa ttcattgctt gacattcttg acggagcagt tcagaaagga    600
ctcaatatcg aggtcccacc atctgtgaac ctcaccatcg acagcgagt caaaaatctg    660 gcttcactga tcgtccaagg agtatctaac aagcttttta aggcacatga tcatgttatc    720
gatccaatca acgagagagc ccgtaattat cttgagcagc tcagccaatc cttcgtattg    780
ctagacatcg tccgtgagaa gaaaacgtgg gtcatagaga agtcaaacga gctctccaca    840
tctgtctttg atttcaagaa aacacttgag gaagaggcac aaaaatacaa agttgctcca    900
gaagagatgt tgatgaaaca cattcaatca acctccgagc aactctcaac acaacttcaa    960
```

```
tcattgcgtg agaagggaca aaacgttttc ggtgatggaa ctaagattga ctccaccatt    1020
gactacttgg agaacttgaa gaagaacttc acagatgctg aggatgttta caaagtccgc    1080
gacgaggttc tgaacgaggg acgtcaacgg atcgccgagc tttcaacctg gacgactagc    1140
cttttgatta tctcggccga atggcaattt gaacctgaag atctactaat cgaagagctc    1200
tacttcgatg cgccaccgcc agttcgcaca agaaacttgt ataggaatcg tgcctaa      1257
```

<210> SEQ ID NO 4
<211> LENGTH: 418
<212> TYPE: PRT
<213> ORGANISM: Artificial Sequence
<220> FEATURE:
<223> OTHER INFORMATION: MDT-28 protein

<400> SEQUENCE: 4

```
Met Thr Asp Val Glu Gln Pro Val Ser Val Glu Asp Gln Gln Ala Gln
1               5                   10                  15

Ala Gln Ser Tyr Tyr Asp Gln Val Leu Gly Asn Ala Tyr Val Gln Thr
            20                  25                  30

Ala Ile Asn Ala Tyr Thr Lys Thr Lys Glu Phe His Pro Leu Leu Asn
        35                  40                  45

Ser Thr Leu Asn Ser Ala Glu Glu Lys Val Ser Thr Val Gly Asn Tyr
    50                  55                  60

Ala Ala Gln Lys Ala Tyr Asp Gly Tyr Asn Ser Tyr Tyr Val Lys Pro
65                  70                  75                  80

Lys Asn Thr Ala Tyr Glu Ala Val Ser Tyr Gly Thr Glu Arg Ala Lys
                85                  90                  95

Thr Ala Val Glu Ser Gly Lys Gln Ala Ala Ile Val Gly Gly Thr Phe
            100                 105                 110

Gly Ile Gly Ala Ala Val Val Leu Thr Gln Phe Ser Leu Ala Leu Ser
        115                 120                 125

Ala Gly Gly Ala Ala Leu Val Leu Glu Gln Val Asp Ser Ala Lys Lys
    130                 135                 140

Leu Gly Ser Ser Ala Ile Ser Thr Ile Lys Glu Ala Glu Leu Ala Val
145                 150                 155                 160

Glu His Arg Ile Phe Ser Ala Leu His Gln Ala Gln Arg Ile Ala Met
                165                 170                 175

Val Pro Val Glu Lys Ile Thr Glu Asn Thr Asn Ser Leu Leu Asp Ile
            180                 185                 190

Leu Asp Gly Ala Val Gln Lys Gly Leu Asn Ile Glu Val Pro Pro Ser
        195                 200                 205

Val Asn Leu Thr Ile Gly Gln Arg Val Lys Asn Leu Ala Ser Leu Ile
    210                 215                 220

Val Gln Gly Val Ser Asn Lys Leu Phe Lys Ala His Asp His Val Ile
225                 230                 235                 240

Asp Pro Ile Asn Glu Arg Ala Arg Asn Tyr Leu Glu Gln Leu Ser Gln
                245                 250                 255

Ser Phe Val Leu Leu Asp Ile Val Arg Glu Lys Lys Thr Trp Val Ile
            260                 265                 270

Glu Lys Ser Asn Glu Leu Ser Thr Ser Val Phe Asp Phe Lys Lys Thr
        275                 280                 285

Leu Glu Glu Glu Ala Gln Lys Tyr Lys Val Ala Pro Glu Glu Met Leu
    290                 295                 300

Met Lys His Ile Gln Ser Thr Ser Glu Gln Leu Ser Thr Gln Leu Gln
305                 310                 315                 320
```

```
Ser Leu Arg Glu Lys Gly Gln Asn Val Phe Gly Asp Gly Thr Lys Ile
                325                 330                 335

Asp Ser Thr Ile Asp Tyr Leu Glu Asn Leu Lys Lys Asn Phe Thr Asp
            340                 345                 350

Ala Glu Asp Val Tyr Lys Val Arg Asp Glu Val Leu Asn Glu Gly Arg
        355                 360                 365

Gln Arg Ile Ala Glu Leu Ser Thr Trp Thr Thr Ser Leu Leu Ile Ile
    370                 375                 380

Ser Ala Glu Trp Gln Phe Glu Pro Glu Asp Leu Leu Ile Glu Glu Leu
385                 390                 395                 400

Tyr Phe Asp Ala Pro Pro Pro Val Arg Thr Arg Asn Leu Tyr Arg Asn
                405                 410                 415

Arg Ala

<210> SEQ ID NO 5
<211> LENGTH: 1314
<212> TYPE: DNA
<213> ORGANISM: Artificial Sequence
<220> FEATURE:
<223> OTHER INFORMATION: Perilipin-2 gene

<400> SEQUENCE: 5
atggcatccg ttgcagttga tccacaaccg agtgtggtga ctcgggtggt caacctgccc      60
ttggtgagct ccacgtatga cctcatgtcc tcagcctatc tcagtacaaa ggaccagtat     120
ccctacctga gtctgtgtgt gagatggca gagaacggtg tgaagaccat cacctccgtg      180
gccatgacca gtgctctgcc catcatccag aagctagagc cgcaaattgc agttgccaat     240
acctatgcct gtaaggggct agacaggatt gaggagagac tgcctattct gaatcagcca     300
tcaactcaga ttgttgccaa tgccaaaggc gctgtgactg gggcaaaaga tgctgtgacg     360
actactgtga ctggggccaa ggattctgtg ccagcacga tcacaggggt gatggacaag      420
accaaggggg cagtgactgg cagtgtggag aagaccaagt ctgtggtcag tggcagcatt     480
aacacagtct tggggagtcg gatgatgcag ctcgtgagca gtggcgtaga aaatgcactc     540
accaaatcag agctgttggt agaacagtac ctccctctca ctgaggaaga actagaaaaa     600
gaagcaaaaa aagttgaagg atttgatctg gttcagaagc caagttatta tgttagactg     660
ggatccctgt ctaccaagct tcactcccgt gcctaccagc aggctctcag cagggttaaa     720
gaagctaagc aaaaaagcca acagaccatt tctcagctcc attctactgt tcacctgatt     780
gaatttgcca ggaagaatgt gtatagtgcc aatcagaaaa ttcaggatgc tcaggataag     840
ctctacctct catgggtaga gtggaaaagg agcattggat atgatgatac tgatgagtcc     900
cactgtgctg agcacattga gtcacgtact cttgcaattg cccgcaacct gactcagcag     960
ctccagacca cgtgccacac cctcctgtcc aacatccaag gtgtaccaca gaacatccaa    1020
gatcaagcca agcacatggg ggtgatggca ggcgacatct actcagtgtt ccgcaatgct    1080
gcctccttta agaagtgtc tgacagcctc ctcacttcta gcaaggggca gctgcagaaa    1140
atgaaggaat ctttagatga cgtgatggat tatcttgtta acaacacgcc cctcaactgg    1200
ctggtaggtc cctttatcc tcagctgact gagtctcaga tgctcagga ccaaggtgca    1260 gagatggaca agagcagcca ggagacccag cgatctgagc ataaaactca ttaa          1314

<210> SEQ ID NO 6
<211> LENGTH: 437
<212> TYPE: PRT
```

<213> ORGANISM: Artificial Sequence
<220> FEATURE:
<223> OTHER INFORMATION: Perilipin-2 protein

<400> SEQUENCE: 6

```
Met Ala Ser Val Ala Val Asp Pro Gln Pro Ser Val Val Thr Arg Val
1               5                   10                  15

Val Asn Leu Pro Leu Val Ser Ser Thr Tyr Asp Leu Met Ser Ser Ala
            20                  25                  30

Tyr Leu Ser Thr Lys Asp Gln Tyr Pro Tyr Leu Lys Ser Val Cys Glu
        35                  40                  45

Met Ala Glu Asn Gly Val Lys Thr Ile Thr Ser Val Ala Met Thr Ser
50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Ile Glu Glu Arg Leu Pro Ile
                85                  90                  95

Leu Asn Gln Pro Ser Thr Gln Ile Val Ala Asn Ala Lys Gly Ala Val
            100                 105                 110

Thr Gly Ala Lys Asp Ala Val Thr Thr Thr Val Thr Gly Ala Lys Asp
        115                 120                 125

Ser Val Ala Ser Thr Ile Thr Gly Val Met Asp Lys Thr Lys Gly Ala
    130                 135                 140

Val Thr Gly Ser Val Glu Lys Thr Lys Ser Val Val Ser Gly Ser Ile
145                 150                 155                 160

Asn Thr Val Leu Gly Ser Arg Met Met Gln Leu Val Ser Ser Gly Val
                165                 170                 175

Glu Asn Ala Leu Thr Lys Ser Glu Leu Leu Val Glu Gln Tyr Leu Pro
            180                 185                 190

Leu Thr Glu Glu Glu Leu Glu Lys Glu Ala Lys Lys Val Glu Gly Phe
        195                 200                 205

Asp Leu Val Gln Lys Pro Ser Tyr Tyr Val Arg Leu Gly Ser Leu Ser
    210                 215                 220

Thr Lys Leu His Ser Arg Ala Tyr Gln Gln Ala Leu Ser Arg Val Lys
225                 230                 235                 240

Glu Ala Lys Gln Lys Ser Gln Gln Thr Ile Ser Gln Leu His Ser Thr
                245                 250                 255

Val His Leu Ile Glu Phe Ala Arg Lys Asn Val Tyr Ser Ala Asn Gln
            260                 265                 270

Lys Ile Gln Asp Ala Gln Asp Lys Leu Tyr Leu Ser Trp Val Glu Trp
        275                 280                 285

Lys Arg Ser Ile Gly Tyr Asp Asp Thr Asp Glu Ser His Cys Ala Glu
    290                 295                 300

His Ile Glu Ser Arg Thr Leu Ala Ile Ala Arg Asn Leu Thr Gln Gln
305                 310                 315                 320

Leu Gln Thr Thr Cys His Thr Leu Leu Ser Asn Ile Gln Gly Val Pro
                325                 330                 335

Gln Asn Ile Gln Asp Gln Ala Lys His Met Gly Val Met Ala Gly Asp
            340                 345                 350

Ile Tyr Ser Val Phe Arg Asn Ala Ala Ser Phe Lys Glu Val Ser Asp
        355                 360                 365

Ser Leu Leu Thr Ser Ser Lys Gly Gln Leu Gln Lys Met Lys Glu Ser
    370                 375                 380

Leu Asp Asp Val Met Asp Tyr Leu Val Asn Asn Thr Pro Leu Asn Trp
```

385                 390                 395                 400
Leu Val Gly Pro Phe Tyr Pro Gln Leu Thr Glu Ser Gln Asn Ala Gln
                    405                 410                 415

Asp Gln Gly Ala Glu Met Asp Lys Ser Ser Gln Glu Thr Gln Arg Ser
                420                 425                 430

Glu His Lys Thr His
        435

<210> SEQ ID NO 7
<211> LENGTH: 1515
<212> TYPE: DNA
<213> ORGANISM: Artificial Sequence
<220> FEATURE:
<223> OTHER INFORMATION: ATGL gene

<400> SEQUENCE: 7

```
atgtttcccc gcgagaagac gtggaacatc tcgttcgcgg gctgcggctt cctcggcgtc     60
tactacgtcg gcgtggcctc ctgcctccgc gagcacgcgc ccttcctggt ggccaacgcc    120
acgcacatct acggcgcctc ggccggggcg ctcacggcca cggcgctggt caccggggtc    180
tgcctgggtg aggctggtgc caagttcatt gaggtatcta agaggcccg gaagcggttc     240
ctgggccccc tgcaccctc cttcaacctg gtaaagatca tccgcagttt cctgctgaag    300
gtcctgcctg ctgatagcca tgagcatgcc agtgggcgcc tggcatctc cctgaccccgc    360
gtgtcagacg gcgagaatgt cattatatcc cacttcaact ccaaggacga gctcatccag    420
gccaatgtct gcagcggttt catccccgtg tactgtgggc tcatccctcc ctccctccag    480
ggggtgcgct acgtggatgg tggcattttca gacaacctgc cactctatga gcttaagaac    540
accatcacag tgtccccctt ctcgggcgag agtgacatct gtccgcagga cagctccacc    600
aacatccacg agctgcgggt caccaacacc agcatccagt tcaacctgcg caacctctac    660
cgcctctcca aggccctctt cccgccgag ccctggtgc tgcgagagat gtgcaagcag    720
ggataccggg atggcctgcg ctttctgcag cggaacggcc tcctgaaccg gcccaacccc    780
ttgctggcgt tgccccccgc cgccccccac ggcccagagg acaaggacca ggcagtggag    840
agcgcccaag cggaggatta ctcgcagctg cccggagaag atcacatcct ggagcacctg    900
cccgccggc tcaatgaggc cctgctggag gctgcgtgg agcccacgga cctgctgacc    960
accctctcca acatgctgcc tgtgcgtctg gccacggcca tgatggtgcc ctacacgctg   1020
ccgctggaga gcgctctgtc cttcaccatc cgcttgctgg agtggctgcc cgacgttccc   1080
gaggacatcc ggtggatgaa ggagcagacg ggcagcatct gccagtacct ggtgatgcgc   1140
gccaagagga agctgggcag gcacctgccc tccaggctgc cggagcaggt ggagctgcgc   1200
cgcgtccagt cgctgcgtc cgtgccgctg tcctgcgccg cctacagaga ggcactgccc   1260
ggctggatgc gcaacaacct ctcgctgggg gacgcgctgg ccaagtggga ggagtgccag   1320
cgccagctgt gctcggcct cttctgcacc aacgtggcct tcccgcccga gctctcgcgc   1380
atgcgcgcac ccgccgaccc ggctcccgcc ccgcggacc cagcatcccc gcagcaccag   1440
ctggccgggc ctgccccctt gctgagcacc cctgctcccg aggcccggcc cgtgatcggg   1500
gccctggggc tgtga                                                   1515
```

<210> SEQ ID NO 8
<211> LENGTH: 504
<212> TYPE: PRT
<213> ORGANISM: Artificial Sequence
<220> FEATURE:

<223> OTHER INFORMATION: ATGL protein

<400> SEQUENCE: 8

```
Met Phe Pro Arg Glu Lys Thr Trp Asn Ile Ser Phe Ala Gly Cys Gly
1               5                   10                  15

Phe Leu Gly Val Tyr Tyr Val Gly Val Ala Ser Cys Leu Arg Glu His
            20                  25                  30

Ala Pro Phe Leu Val Ala Asn Ala Thr His Ile Tyr Gly Ala Ser Ala
        35                  40                  45

Gly Ala Leu Thr Ala Thr Ala Leu Val Thr Gly Val Cys Leu Gly Glu
    50                  55                  60

Ala Gly Ala Lys Phe Ile Glu Val Ser Lys Glu Ala Arg Lys Arg Phe
65                  70                  75                  80

Leu Gly Pro Leu His Pro Ser Phe Asn Leu Val Lys Ile Ile Arg Ser
                85                  90                  95

Phe Leu Leu Lys Val Leu Pro Ala Asp Ser His Glu His Ala Ser Gly
            100                 105                 110

Arg Leu Gly Ile Ser Leu Thr Arg Val Ser Asp Gly Glu Asn Val Ile
        115                 120                 125

Ile Ser His Phe Asn Ser Lys Asp Glu Leu Ile Gln Ala Asn Val Cys
130                 135                 140

Ser Gly Phe Ile Pro Val Tyr Cys Gly Leu Ile Pro Pro Ser Leu Gln
145                 150                 155                 160

Gly Val Arg Tyr Val Asp Gly Gly Ile Ser Asp Asn Leu Pro Leu Tyr
                165                 170                 175

Glu Leu Lys Asn Thr Ile Thr Val Ser Pro Phe Ser Gly Glu Ser Asp
            180                 185                 190

Ile Cys Pro Gln Asp Ser Ser Thr Asn Ile His Glu Leu Arg Val Thr
        195                 200                 205

Asn Thr Ser Ile Gln Phe Asn Leu Arg Asn Leu Tyr Arg Leu Ser Lys
210                 215                 220

Ala Leu Phe Pro Pro Glu Pro Leu Val Leu Arg Glu Met Cys Lys Gln
225                 230                 235                 240

Gly Tyr Arg Asp Gly Leu Arg Phe Leu Gln Arg Asn Gly Leu Leu Asn
                245                 250                 255

Arg Pro Asn Pro Leu Leu Ala Leu Pro Pro Ala Arg Pro His Gly Pro
            260                 265                 270

Glu Asp Lys Asp Gln Ala Val Glu Ser Ala Gln Ala Glu Asp Tyr Ser
        275                 280                 285

Gln Leu Pro Gly Glu Asp His Ile Leu Glu His Leu Pro Ala Arg Leu
    290                 295                 300

Asn Glu Ala Leu Leu Glu Ala Cys Val Glu Pro Thr Asp Leu Leu Thr
305                 310                 315                 320

Thr Leu Ser Asn Met Leu Pro Val Arg Leu Ala Thr Ala Met Met Val
                325                 330                 335

Pro Tyr Thr Leu Pro Leu Glu Ser Ala Leu Ser Phe Thr Ile Arg Leu
            340                 345                 350

Leu Glu Trp Leu Pro Asp Val Pro Glu Asp Ile Arg Trp Met Lys Glu
        355                 360                 365

Gln Thr Gly Ser Ile Cys Gln Tyr Leu Val Met Arg Ala Lys Arg Lys
    370                 375                 380

Leu Gly Arg His Leu Pro Ser Arg Leu Pro Glu Gln Val Glu Leu Arg
385                 390                 395                 400
```

```
Arg Val Gln Ser Leu Pro Ser Val Pro Leu Ser Cys Ala Ala Tyr Arg
            405                 410                 415

Glu Ala Leu Pro Gly Trp Met Arg Asn Asn Leu Ser Leu Gly Asp Ala
        420                 425                 430

Leu Ala Lys Trp Glu Glu Cys Gln Arg Gln Leu Leu Leu Gly Leu Phe
    435                 440                 445

Cys Thr Asn Val Ala Phe Pro Pro Glu Ala Leu Arg Met Arg Ala Pro
450                 455                 460

Ala Asp Pro Ala Pro Ala Pro Asp Pro Ala Ser Pro Gln His Gln
465                 470                 475                 480

Leu Ala Gly Pro Ala Pro Leu Leu Ser Thr Pro Ala Pro Glu Ala Arg
                485                 490                 495

Pro Val Ile Gly Ala Leu Gly Leu
            500
```

<210> SEQ ID NO 9
<211> LENGTH: 1563
<212> TYPE: DNA
<213> ORGANISM: Artificial Sequence
<220> FEATURE:
<223> OTHER INFORMATION: MLDS-GFP fusion gene

<400> SEQUENCE: 9

```
atgactgacc agaagaccat cgacagcgtc aagacctcgc tgtacgcggc cgtaggcgcc      60
ggagacgtcg tcgtgcaggc cgtggccgac gtcgtcgccc aggtccgctc gcgcgccgag     120
tccacccagg gtgacgtcga agagcgtgtc ggcggcgcca aggagcgcat cgccggactc     180
caggaagagg tcaccgaggg tgtcgagaac cttcgcgacc gcctcgccgg actgccgtcc     240
gagctgcccg aggagcttgc cgagctgcgt gagaagttca ccgccgacga gctgcgcaag     300
gttgccgagg cctacctgaa ggtcgcctcc gacctgtaca cgtcgctcgc cgagcgcggc     360
gaggacaccg tcgagcgcat ccgcaagcag ccggtcgtcg aggagggcat cggccgcgcc     420
gagaccgcct tcggtgacgc cgtcgagctg accgaggaag ctctcggcac cgttgcacgc     480
cagacgcgcg ccgtcggcga gcaggccgca aagctcgcgg gccgcgcttc gggtcgcatc     540
tccgacaccg ccgagggact cggcgaggcc atcgccgacg ccggcgacga ggctgccctg     600
aaggttctcg acctgggcga ccaggccgag gaagcgtcga aggacgctgc cgatcgcgtc     660
accgccaccg cggccgacgt ccaggctcgc gccgacaagg ctgccccggc caagcacgcc     720
gctcccgcga agaaggctgc tccggccaag gctgcggcaa ccccggcccc ggccccggcc     780
aagaaggcca ccgctccggc caagaaggct gctccggcca agaaggctaa gcttgcggcc     840
gcaatggtga gcaagggcga ggagctgttc accggggtgg tgcccatcct ggtcgagctg     900
gacggcgacg taaacggcca caagttcagc gtgtccggcg agggcgaggg cgatgccacc     960
tacggcaagc tgaccctgaa gttcatctgc accaccggca agctgcccgt gccctggccc    1020
accctcgtga ccaccctgac ctacggcgtg cagtgcttca gccgctaccc cgaccacatg    1080
aagcagcacg acttcttcaa gtccgccatg cccgaaggct acgtccagga gcgcaccatc    1140
ttcttcaagg acgacggcaa ctacaagacc cgcgccgagg tgaagttcga gggcgacacc    1200
ctggtgaacc gcatcgagct gaagggcatc gacttcaagg aggacggcaa catcctgggg    1260
cacaagctgg agtacaacta caacagccac aacgtctata tcatggccga caagcagaag    1320
aacggcatca aggtgaactt caagatccgc cacaacatcg aggacggcag cgtgcagctc    1380
gccgaccact accagcagaa caccccatc ggcgacggcc ccgtgctgct gcccgacaac    1440
```
cactacctga gcacccagtc cgccctgagc aaagacccca acgagaagcg cgatcacatg    1500
gtcctgctgg agttcgtgac cgccgccggg atcactctcg gcatggacga gctgtacaag    1560
taa                                                                 1563

<210> SEQ ID NO 10
<211> LENGTH: 520
<212> TYPE: PRT
<213> ORGANISM: Artificial Sequence
<220> FEATURE:
<223> OTHER INFORMATION: MLDS-GFP fusion protein

<400> SEQUENCE: 10

```
Met Thr Asp Gln Lys Thr Ile Asp Ser Val Lys Thr Ser Leu Tyr Ala
1               5                   10                  15

Ala Val Gly Ala Gly Asp Val Val Gln Ala Val Ala Asp Val Val
            20                  25                  30

Ala Gln Val Arg Ser Arg Ala Glu Ser Thr Gln Gly Asp Val Glu Glu
        35                  40                  45

Arg Val Gly Gly Ala Lys Glu Arg Ile Ala Gly Leu Gln Glu Val
    50                  55                  60

Thr Glu Gly Val Glu Asn Leu Arg Asp Arg Leu Ala Gly Leu Pro Ser
65                  70                  75                  80

Glu Leu Pro Glu Glu Leu Ala Glu Leu Arg Glu Lys Phe Thr Ala Asp
                85                  90                  95

Glu Leu Arg Lys Val Ala Glu Ala Tyr Leu Lys Val Ala Ser Asp Leu
            100                 105                 110

Tyr Thr Ser Leu Ala Glu Arg Gly Glu Asp Thr Val Glu Arg Ile Arg
        115                 120                 125

Lys Gln Pro Val Val Glu Glu Gly Ile Gly Arg Ala Glu Thr Ala Phe
    130                 135                 140

Gly Asp Ala Val Glu Leu Thr Glu Glu Ala Leu Gly Thr Val Ala Arg
145                 150                 155                 160

Gln Thr Arg Ala Val Gly Glu Gln Ala Ala Lys Leu Ala Gly Arg Ala
                165                 170                 175

Ser Gly Arg Ile Ser Asp Thr Ala Glu Gly Leu Gly Glu Ala Ile Ala
            180                 185                 190

Asp Ala Gly Asp Glu Ala Ala Leu Lys Val Leu Asp Leu Gly Asp Gln
        195                 200                 205

Ala Glu Glu Ala Ser Lys Asp Ala Ala Asp Arg Val Thr Ala Thr Ala
    210                 215                 220

Ala Asp Val Gln Ala Arg Ala Asp Lys Ala Ala Pro Ala Lys His Ala
225                 230                 235                 240

Ala Pro Ala Lys Lys Ala Ala Pro Ala Lys Ala Ala Thr Pro Ala
                245                 250                 255

Pro Ala Pro Ala Lys Lys Ala Ala Pro Ala Lys Lys Ala Ala Pro
            260                 265                 270

Ala Lys Lys Ala Lys Leu Ala Ala Ala Met Val Ser Lys Gly Glu Glu
        275                 280                 285

Leu Phe Thr Gly Val Val Pro Ile Leu Val Glu Leu Asp Gly Asp Val
    290                 295                 300

Asn Gly His Lys Phe Ser Val Ser Gly Glu Gly Glu Gly Asp Ala Thr
305                 310                 315                 320

Tyr Gly Lys Leu Thr Leu Lys Phe Ile Cys Thr Thr Gly Lys Leu Pro
                325                 330                 335
```

| | | | | | | | | | | | |
|---|---|---|---|---|---|---|---|---|---|---|---|
|Val|Pro|Trp|Pro|Thr|Leu|Val|Thr|Thr|Leu|Thr|Tyr|Gly|Val|Gln|Cys|
| | | |340| | | |345| | | | |350| | | |

Phe Ser Arg Tyr Pro Asp His Met Lys Gln His Asp Phe Phe Lys Ser
        355                 360                 365

Ala Met Pro Glu Gly Tyr Val Gln Glu Arg Thr Ile Phe Phe Lys Asp
    370                 375                 380

Asp Gly Asn Tyr Lys Thr Arg Ala Glu Val Lys Phe Glu Gly Asp Thr
385                 390                 395                 400

Leu Val Asn Arg Ile Glu Leu Lys Gly Ile Asp Phe Lys Glu Asp Gly
                405                 410                 415

Asn Ile Leu Gly His Lys Leu Glu Tyr Asn Tyr Asn Ser His Asn Val
            420                 425                 430

Tyr Ile Met Ala Asp Lys Gln Lys Asn Gly Ile Lys Val Asn Phe Lys
        435                 440                 445

Ile Arg His Asn Ile Glu Asp Gly Ser Val Gln Leu Ala Asp His Tyr
    450                 455                 460

Gln Gln Asn Thr Pro Ile Gly Asp Gly Pro Val Leu Leu Pro Asp Asn
465                 470                 475                 480

His Tyr Leu Ser Thr Gln Ser Ala Leu Ser Lys Asp Pro Asn Glu Lys
                485                 490                 495

Arg Asp His Met Val Leu Leu Glu Phe Val Thr Ala Ala Gly Ile Thr
            500                 505                 510

Leu Gly Met Asp Glu Leu Tyr Lys
        515                 520

```
<210> SEQ ID NO 11
<211> LENGTH: 1980
<212> TYPE: DNA
<213> ORGANISM: Artificial Sequence
<220> FEATURE:
<223> OTHER INFORMATION: MDT-28-GFP fusion gene

<400> SEQUENCE: 11
atgactgacg tcgagcagcc agtatcagtt gaggatcaac aagcccaagc ccaaagctac      60
tacgatcaag tcttaggaaa tgcttacgta caaacggcaa tcaatgcata cacaaagact     120
aaagagttcc atccacttct taactccaca ttgaattcag ccgaagaaaa ggtttccact     180
gtcggaaatt atgcggctca aaaagcctat gacggataca attcgtacta cgttaagcca     240
aagaacaccg cttatgaagc agtctcttat ggaaccgaga gggccaaaac agctgttgag     300
agcggaaagc aagctgctat cgttggtggt acattcggaa ttggagctgc cgtcgttttg     360
acccaattct cacttgcctt gagtgctgga ggtgccgccc tggtccttga gcaagtggac     420
agtgctaaaa agttgggaag cagcgcgatt tctacgatca agaagccga gcttgctgtc      480 gaacacagaa tcttctcagc tcttcatcag gcccaacgaa tcgccatggt tcctgtggag     540
aaaatcacag aaatactaa ttcattgctt gacattcttg acggagcagt tcagaaagga      600
ctcaatatcg aggtcccacc atctgtgaac ctcaccatcg acagcgagt caaaaatctg      660 gcttcactga tcgtccaagg agtatctaac aaggcacatg atcatgttat cgatccaatc     720
aacgagagag cccgtaatta tcttgagcag ctcagccaat ccttcgtatt gctagacatc     780
gtccgtgaga agaaaacgtg ggtcatagag aagtcaaacg agctctccac atctgtcttt     840
gatttcaaga aaacacttga ggaagaggca caaaaataca agttgctcc agaagagatg      900 ttgatgaaac acattcaatc aacctccgag caactctcaa cacaacttca atcattgcgt     960
gagaagggac aaaacgtttt cggtgatgga actaagattg actccaccat tgactacttg    1020
```

```
gagaacttga agaagaactt cacagatgct gaggatgttt acaaagtccg cgacgaggtt    1080
ctgaacgagg gacgtcaacg gatcgccgag ctttcaacct ggacgactag ccttttgatt    1140
atctcggccg aatggcaatt tgaacctgaa gatctactaa tcgaagagct ctacttcgat    1200
gcgccaccgc cagttcgcac aagaaacttg tataggaatc gtgccaagct tgcggccgca    1260
atggtgagca agggcgagga gctgttcacc ggggtggtgc ccatcctggt cgagctggac    1320
ggcgacgtaa acggccacaa gttcagcgtg tccggcgagg gcgagggcga tgccacctac    1380
ggcaagctga cc ctgaagtt catctgcacc accggcaagc tgcccgtgcc ctggcccacc    1440
ctcgtgacca ccctgaccta cggcgtgcag tgcttcagcc gctaccccga ccacatgaag    1500
cagcacgact tcttcaagtc cgccatgccc gaaggctacg tccaggagcg caccatcttc    1560
ttcaaggacg acggcaacta caagacccgc gccgaggtga agttcgaggg cgacaccctg    1620
gtgaaccgca tcgagctgaa gggcatcgac ttcaaggagg acggcaacat cctggggcac    1680
aagctggagt acaactacaa cagccacaac gtctatatca tggccgacaa gcagaagaac    1740
ggcatcaagg tgaacttcaa gatccgccac aacatcgagg acggcagcgt gcagctcgcc    1800
gaccactacc agcagaacac ccccatcggc gacggccccg tgctgctgcc cgacaaccac    1860
tacctgagca cccagtccgc cctgagcaaa gaccccaacg agaagcgcga tcacatggtc    1920
ctgctggagt tcgtgaccgc cgccgggatc actctcggca tggacgagct gtacaagtaa    1980
```

<210> SEQ ID NO 12
<211> LENGTH: 659
<212> TYPE: PRT
<213> ORGANISM: Artificial Sequence
<220> FEATURE:
<223> OTHER INFORMATION: MDT-28-GFP fuion protein

<400> SEQUENCE: 12

```
Met Thr Asp Val Glu Gln Pro Val Ser Val Glu Asp Gln Gln Ala Gln
1               5                   10                  15

Ala Gln Ser Tyr Tyr Asp Gln Val Leu Gly Asn Ala Tyr Val Gln Thr
            20                  25                  30

Ala Ile Asn Ala Tyr Thr Lys Thr Lys Glu Phe His Pro Leu Leu Asn
        35                  40                  45

Ser Thr Leu Asn Ser Ala Glu Glu Lys Val Ser Thr Val Gly Asn Tyr
    50                  55                  60

Ala Ala Gln Lys Ala Tyr Asp Gly Tyr Asn Ser Tyr Tyr Val Lys Pro
65                  70                  75                  80

Lys Asn Thr Ala Tyr Glu Ala Val Ser Tyr Gly Thr Glu Arg Ala Lys
                85                  90                  95

Thr Ala Val Glu Ser Gly Lys Gln Ala Ala Ile Val Gly Gly Thr Phe
            100                 105                 110

Gly Ile Gly Ala Ala Val Val Leu Thr Gln Phe Ser Leu Ala Leu Ser
        115                 120                 125

Ala Gly Gly Ala Ala Leu Val Leu Glu Gln Val Asp Ser Ala Lys Lys
    130                 135                 140

Leu Gly Ser Ser Ala Ile Ser Thr Ile Lys Glu Ala Glu Leu Ala Val
145                 150                 155                 160

Glu His Arg Ile Phe Ser Ala Leu His Gln Ala Gln Arg Ile Ala Met
                165                 170                 175

Val Pro Val Glu Lys Ile Thr Glu Asn Thr Asn Ser Leu Leu Asp Ile
            180                 185                 190
```

```
Leu Asp Gly Ala Val Gln Lys Gly Leu Asn Ile Glu Val Pro Pro Ser
            195                 200                 205

Val Asn Leu Thr Ile Gly Gln Arg Val Lys Asn Leu Ala Ser Leu Ile
        210                 215                 220

Val Gln Gly Val Ser Asn Lys Ala His Asp His Val Ile Asp Pro Ile
225                 230                 235                 240

Asn Glu Arg Ala Arg Asn Tyr Leu Glu Gln Leu Ser Gln Ser Phe Val
                245                 250                 255

Leu Leu Asp Ile Val Arg Glu Lys Lys Thr Trp Val Ile Glu Lys Ser
            260                 265                 270

Asn Glu Leu Ser Thr Ser Val Phe Asp Phe Lys Lys Thr Leu Glu Glu
        275                 280                 285

Glu Ala Gln Lys Tyr Lys Val Ala Pro Glu Glu Met Leu Met Lys His
    290                 295                 300

Ile Gln Ser Thr Ser Glu Gln Leu Ser Thr Gln Leu Gln Ser Leu Arg
305                 310                 315                 320

Glu Lys Gly Gln Asn Val Phe Gly Asp Gly Thr Lys Ile Asp Ser Thr
                325                 330                 335

Ile Asp Tyr Leu Glu Asn Leu Lys Lys Asn Phe Thr Asp Ala Glu Asp
            340                 345                 350

Val Tyr Lys Val Arg Asp Glu Val Leu Asn Glu Gly Arg Gln Arg Ile
        355                 360                 365

Ala Glu Leu Ser Thr Trp Thr Thr Ser Leu Leu Ile Ile Ser Ala Glu
    370                 375                 380

Trp Gln Phe Glu Pro Glu Asp Leu Leu Ile Glu Glu Leu Tyr Phe Asp
385                 390                 395                 400

Ala Pro Pro Val Arg Thr Arg Asn Leu Tyr Arg Asn Arg Ala Lys
                405                 410                 415

Leu Ala Ala Ala Met Val Ser Lys Gly Glu Glu Leu Phe Thr Gly Val
            420                 425                 430

Val Pro Ile Leu Val Glu Leu Asp Gly Asp Val Asn Gly His Lys Phe
        435                 440                 445

Ser Val Ser Gly Glu Gly Glu Gly Asp Ala Thr Tyr Gly Lys Leu Thr
    450                 455                 460

Leu Lys Phe Ile Cys Thr Thr Gly Lys Leu Pro Val Pro Trp Pro Thr
465                 470                 475                 480

Leu Val Thr Thr Leu Thr Tyr Gly Val Gln Cys Phe Ser Arg Tyr Pro
                485                 490                 495

Asp His Met Lys Gln His Asp Phe Phe Lys Ser Ala Met Pro Glu Gly
            500                 505                 510

Tyr Val Gln Glu Arg Thr Ile Phe Phe Lys Asp Asp Gly Asn Tyr Lys
        515                 520                 525

Thr Arg Ala Glu Val Lys Phe Glu Gly Asp Thr Leu Val Asn Arg Ile
    530                 535                 540

Glu Leu Lys Gly Ile Asp Phe Lys Glu Asp Gly Asn Ile Leu Gly His
545                 550                 555                 560

Lys Leu Glu Tyr Asn Tyr Asn Ser His Asn Val Tyr Ile Met Ala Asp
                565                 570                 575

Lys Gln Lys Asn Gly Ile Lys Val Asn Phe Lys Ile Arg His Asn Ile
            580                 585                 590

Glu Asp Gly Ser Val Gln Leu Ala Asp His Tyr Gln Gln Asn Thr Pro
        595                 600                 605

Ile Gly Asp Gly Pro Val Leu Leu Pro Asp Asn His Tyr Leu Ser Thr
```

```
            610                615                620
Gln Ser Ala Leu Ser Lys Asp Pro Asn Glu Lys Arg Asp His Met Val
625                630                635                640

Leu Leu Glu Phe Val Thr Ala Ala Gly Ile Thr Leu Gly Met Asp Glu
            645                650                655

Leu Tyr Lys

<210> SEQ ID NO 13
<211> LENGTH: 2031
<212> TYPE: DNA
<213> ORGANISM: Artificial Sequence
<220> FEATURE:
<223> OTHER INFORMATION: Perilipin-2-GFP fusion gene

<400> SEQUENCE: 13
atggcatccg ttgcagttga tccacaaccg agtgtggtga ctcgggtggt caacctgccc     60
ttggtgagct ccacgtatga cctcatgtcc tcagcctatc tcagtacaaa ggaccagtat    120
ccctacctga agtctgtgtg tgagatggca gagaacggtg tgaagaccat cacctccgtg    180
gccatgacca gtgctctgcc catcatccag aagctagagc gcaaattgc agttgccaat    240 acctatgcct gtaaggggct agacaggatt gaggagagac tgcctattct gaatcagcca    300
tcaactcaga ttgttgccaa tgccaaaggc gctgtgactg ggcaaaaga tgctgtgacg    360 actactgtga ctggggccaa ggattctgtg ccagcacga tcacaggggt gatggacaag    420
accaaagggg cagtgactgg cagtgtggag aagaccaagt ctgtggtcag tggcagcatt    480
aacacagtct ggggagtcg gatgatgcag ctcgtgagca gtggcgtaga aaatgcactc    540
accaaatcag agctgttggt agaacagtac ctccctctca ctgaggaaga actagaaaaa    600
gaagcaaaaa agttgaagg atttgatctg gttcagaagc caagttatta tgttagactg    660
ggatccctgt ctaccaagct tcactcccgt gcctaccagc aggctctcag cagggttaaa    720
gaagctaagc aaaaaagcca acagaccatt tctcagctcc attctactgt tcacctgatt    780
gaatttgcca ggaagaatgt gtatagtgcc aatcagaaaa ttcaggatgc tcaggataag    840
ctctacctct catgggtaga gtggaaaagg agcattggat atgatgatac tgatgagtcc    900
cactgtgctg agcacattga gtcacgtact cttgcaattg cccgcaacct gactcagcag    960
ctccagacca cgtgccacac cctcctgtcc aacatccaag gtgtaccaca gaacatccaa   1020
gatcaagcca agcacatggg ggtgatggca ggcgacatct actcagtgtt ccgcaatgct   1080
gcctccttta agaagtgtc tgacagcctc tcacttcta gcaaggggca gctgcagaaa   1140
atgaaggaat cttagatga cgtgatggat tatcttgtta caacacgcc cctcaactgg   1200 ctggtaggtc ccttttatcc tcagctgact gagtctcaga atgctcagga ccaaggtgca   1260
gagatggaca agagcagcca ggagacccag cgatctgagc ataaaactca tatggtgagc   1320
aagggcgagg agctgttcac cggggtggtg cccatcctgg tcgagctgga cggcgacgta   1380
aacggccaca gttcagcgt gtccggcgag ggcgagggcg atgccaccta cggcaagctg   1440
accctgaagt tcatctgcac caccggcaag ctgcccgtgc cctggcccac cctcgtgacc   1500
accctgacct acggcgtgca gtgcttcagc cgctaccccg accacatgaa gcagcacgac   1560
ttcttcaagt ccgccatgcc cgaaggctac gtccaggagc gcaccatctt cttcaaggac   1620
gacggcaact acaagacccg cgccgaggtg aagttcgagg gcgacaccct ggtgaaccgc   1680
atcgagctga agggcatcga cttcaaggag gacggcaaca tcctggggca caagctggag   1740
tacaactaca acagccacaa cgtctatatc atggccgaca agcagaagaa cggcatcaag   1800
```

```
gtgaacttca agatccgcca caacatcgag gacggcagcg tgcagctcgc cgaccactac    1860
cagcagaaca cccccatcgg cgacggcccc gtgctgctgc ccgacaacca ctacctgagc    1920
acccagtccg ccctgagcaa agaccccaac gagaagcgcg atcacatggt cctgctggag    1980
ttcgtgaccg ccgccgggat cactctcggc atggacgagc tgtacaagta a             2031
```

<210> SEQ ID NO 14
<211> LENGTH: 676
<212> TYPE: PRT
<213> ORGANISM: Artificial Sequence
<220> FEATURE:
<223> OTHER INFORMATION: Perilipin-2-GFP fusion protein

<400> SEQUENCE: 14

```
Met Ala Ser Val Ala Val Asp Pro Gln Pro Ser Val Val Thr Arg Val
1               5                   10                  15

Val Asn Leu Pro Leu Val Ser Ser Thr Tyr Asp Leu Met Ser Ser Ala
            20                  25                  30

Tyr Leu Ser Thr Lys Asp Gln Tyr Pro Tyr Leu Lys Ser Val Cys Glu
        35                  40                  45

Met Ala Glu Asn Gly Val Lys Thr Ile Thr Ser Val Ala Met Thr Ser
    50                  55                  60

Ala Leu Pro Ile Ile Gln Lys Leu Glu Pro Gln Ile Ala Val Ala Asn
65                  70                  75                  80

Thr Tyr Ala Cys Lys Gly Leu Asp Arg Ile Glu Glu Arg Leu Pro Ile
                85                  90                  95

Leu Asn Gln Pro Ser Thr Gln Ile Val Ala Asn Ala Lys Gly Ala Val
            100                 105                 110

Thr Gly Ala Lys Asp Ala Val Thr Thr Thr Val Thr Gly Ala Lys Asp
        115                 120                 125

Ser Val Ala Ser Thr Ile Thr Gly Val Met Asp Lys Thr Lys Gly Ala
    130                 135                 140

Val Thr Gly Ser Val Glu Lys Thr Lys Ser Val Val Ser Gly Ser Ile
145                 150                 155                 160

Asn Thr Val Leu Gly Ser Arg Met Met Gln Leu Val Ser Ser Gly Val
                165                 170                 175

Glu Asn Ala Leu Thr Lys Ser Glu Leu Leu Val Glu Gln Tyr Leu Pro
            180                 185                 190

Leu Thr Glu Glu Glu Leu Glu Lys Glu Ala Lys Lys Val Glu Gly Phe
        195                 200                 205

Asp Leu Val Gln Lys Pro Ser Tyr Tyr Val Arg Leu Gly Ser Leu Ser
    210                 215                 220

Thr Lys Leu His Ser Arg Ala Tyr Gln Gln Ala Leu Ser Arg Val Lys
225                 230                 235                 240

Glu Ala Lys Gln Lys Ser Gln Gln Thr Ile Ser Gln Leu His Ser Thr
                245                 250                 255

Val His Leu Ile Glu Phe Ala Arg Lys Asn Val Tyr Ser Ala Asn Gln
            260                 265                 270

Lys Ile Gln Asp Ala Gln Asp Lys Leu Tyr Leu Ser Trp Val Glu Trp
        275                 280                 285

Lys Arg Ser Ile Gly Tyr Asp Asp Thr Asp Glu Ser His Cys Ala Glu
    290                 295                 300

His Ile Glu Ser Arg Thr Leu Ala Ile Ala Arg Asn Leu Thr Gln Gln
305                 310                 315                 320
```

```
Leu Gln Thr Thr Cys His Thr Leu Leu Ser Asn Ile Gln Gly Val Pro
                325                 330                 335

Gln Asn Ile Gln Asp Gln Ala Lys His Met Gly Val Met Ala Gly Asp
            340                 345                 350

Ile Tyr Ser Val Phe Arg Asn Ala Ala Ser Phe Lys Glu Val Ser Asp
        355                 360                 365

Ser Leu Leu Thr Ser Ser Lys Gly Gln Leu Gln Lys Met Lys Glu Ser
    370                 375                 380

Leu Asp Asp Val Met Asp Tyr Leu Val Asn Asn Thr Pro Leu Asn Trp
385                 390                 395                 400

Leu Val Gly Pro Phe Tyr Pro Gln Leu Thr Glu Ser Gln Asn Ala Gln
                405                 410                 415

Asp Gln Gly Ala Glu Met Asp Lys Ser Ser Gln Glu Thr Gln Arg Ser
            420                 425                 430

Glu His Lys Thr His Met Val Ser Lys Gly Glu Leu Phe Thr Gly
        435                 440                 445

Val Val Pro Ile Leu Val Glu Leu Asp Gly Asp Val Asn Gly His Lys
    450                 455                 460

Phe Ser Val Ser Gly Glu Gly Glu Gly Asp Ala Thr Tyr Gly Lys Leu
465                 470                 475                 480

Thr Leu Lys Phe Ile Cys Thr Thr Gly Lys Leu Pro Val Pro Trp Pro
                485                 490                 495

Thr Leu Val Thr Thr Leu Thr Tyr Gly Val Gln Cys Phe Ser Arg Tyr
            500                 505                 510

Pro Asp His Met Lys Gln His Asp Phe Phe Lys Ser Ala Met Pro Glu
        515                 520                 525

Gly Tyr Val Gln Glu Arg Thr Ile Phe Phe Lys Asp Asp Gly Asn Tyr
    530                 535                 540

Lys Thr Arg Ala Glu Val Lys Phe Glu Gly Asp Thr Leu Val Asn Arg
545                 550                 555                 560

Ile Glu Leu Lys Gly Ile Asp Phe Lys Glu Asp Gly Asn Ile Leu Gly
                565                 570                 575

His Lys Leu Glu Tyr Asn Tyr Asn Ser His Asn Val Tyr Ile Met Ala
            580                 585                 590

Asp Lys Gln Lys Asn Gly Ile Lys Val Asn Phe Lys Ile Arg His Asn
        595                 600                 605

Ile Glu Asp Gly Ser Val Gln Leu Ala Asp His Tyr Gln Gln Asn Thr
    610                 615                 620

Pro Ile Gly Asp Gly Pro Val Leu Leu Pro Asp Asn His Tyr Leu Ser
625                 630                 635                 640

Thr Gln Ser Ala Leu Ser Lys Asp Pro Asn Glu Lys Arg Asp His Met
                645                 650                 655

Val Leu Leu Glu Phe Val Thr Ala Ala Gly Ile Thr Leu Gly Met Asp
            660                 665                 670

Glu Leu Tyr Lys
    675
```

PREPARATION METHOD OF ADIPOSOMES, AND USE THEREOF

CROSS-REFERENCE TO RELATED APPLICATIONS

The present application is a U.S. National Phase of International Patent Application Serial No. PCT/CN2016/106732, entitled "PREPARATION METHOD OF LIPID BODIES, AND USE THEREOF," filed on Nov. 22, 2016. International Patent Application Serial No. PCT/CN2016/106732 claims priority to Chinese Patent Application No. 201510974956.6, filed on Dec. 23, 2015. The entire contents of each of the above-cited applications are hereby incorporated by reference in their entirety for all purposes.

THE FIELD OF INVENTION

The present invention is related to the field of biotechnology, in particular to a preparation method of adiposomes and use thereof.

SEQUENCE LISTING

A Sequence Listing submitted as an ASCII text file via EFS-Web is hereby incorporated by reference in accordance with 35 U.S.C. 1.52(e). The name of the ASCII text file for the Sequence Listing is Substitute Sequence Listing JEE18305PCTUS.txt, the date of creation of the ASCII text file is Nov. 16, 2018, and the size of the ASCII text file is 43.152 KB. The material in this submitted text file is hereby incorporated by reference in its entirety into this application.

THE BACKGROUND

A lipid droplet (LD) is a cellular organelle that consists of a neutral lipid core, a monolayer phospholipid membrane and associated proteins, and the functions of such cellular organelle include: 1) synthesis, storage, metabolization and transportation of lipids; 2) storage and degradation of proteins; 3) production and modification of lipid signaling molecules and hormones; and 4) interaction with other cellular organelles. Because the lipid droplets have the above-mentioned multiple functions, many human diseases, especially metabolic diseases, are closely related to the formation and dynamic changes of lipid droplets. However, the formation mechanism and dynamic changes of the lipid droplets are still difficult to study. Currently, there is still a lack of comprehensive understanding of how lipid droplets are formed, of the functions of lipid droplets and of their regulatory mechanisms. It is the complexities of the composition of lipid droplets and their interaction with other cellular organelles that interfere with our ability to dissect these mechanisms.

In the past decade, people have been dedicated to the isolation and purification of lipid droplets, and to the elucidation of the protein and lipid composition of lipid droplets through proteomic and lipidomic studies. However, it is found in the studies of proteomes and other components that lipid droplets obtained by isolation almost always contain fragments of the endoplasmic reticulum, mitochondria, and other cellular organelles. It can be seen that it is necessary to prepare artificial lipid droplets (ALDs) which are close to the natural lipid droplets in both structure and composition.

In addition to lipid droplets, there is a type of structure in the human body that is constructed by a monolayer phospholipid membrane packaging neutral lipids and is coated with proteins on its surface, and such structure is called a lipoprotein. Although the structure of the lipoprotein is very similar to that of the lipid droplet, they are different in localization and surface proteins: lipid droplets are present in cells, but lipoproteins are present in blood; the main protein on lipid droplets is a lipid droplet resident/structural protein, but the main protein on lipoproteins is an apolipoprotein. Different lipoproteins have different apolipoproteins on their surface. The type and ratio of lipoproteins have a very important impact on human health. A high-density lipoprotein (HDL) is a key component of cholesterol reverse transport, which can prevent the deposition of cholesterol on vascular walls, having a very important preventive effect on cardiac and cerebral vessel diseases, such as atherosclerosis. Artificial lipoproteins may be used for supplements of high-density lipoproteins or other drug carriers.

THE SUMMARY OF INVENTION

The problems to be solved by the present invention are to provide a drug carrier and a system for studying lipid droplets in vitro.

To address the above problems, the invention first provides a preparation method of adiposomes which consist of neutral lipids and a monolayer phospholipid membrane.

The method for preparing adiposomes provided by the present invention comprises the following steps: a1) vortexing phospholipids and neutral lipids in a buffer to enable a reaction between both, then performing centrifugation, collecting an upper liquid phase, and obtaining the adiposomes by isolation of the upper liquid phase.

The "obtaining the adiposomes by isolation of the upper liquid phase" may comprise the following steps: a2) performing purification on the upper liquid phase for twice or more, wherein the process of each purification can be: uniformly mixing the upper liquid phase with the buffer, followed by layering the mixture, and collecting an upper liquid phase; and a3) uniformly mixing the upper liquid phase obtained in step a2) with the buffer, layering the mixture, and collecting a lower liquid phase in which the adiposomes are contained.

The buffer may be buffer B.

Solutes of the buffer B and their concentrations in the buffer may be: 15 mM-25 mM HEPES, 80 mM~120 mM KCl, 1.5~2.5 mM $MgCl_2$; and solvent may be deionized water; and pH may be 7.2~7.6.

The solutes of the buffer B and their concentrations in the buffer may particularly be: 20 mM HEPES, 100 mM KCl, 2 mM $MgCl_2$; and the solvent may particularly be deionized water; and pH may particularly be 7.4.

In the step a1), the parameter of the vortexing may be: a total time of 3~5 min. In the step a1), the parameters of the centrifugation may be: 18000~22000 g, 3~7 min. In the step a1), the parameter of the vortexing may particularly be: a total time of 4 min. In the step a1), the parameters of the centrifugations may particularly be: 20000 g, 5 min.

In the step a2), the number of times in the step of "performing purification on the upper liquid phase for twice or more" is controlled based on that there is no precipitate after uniformly mixing and layering the upper liquid phase and buffer. In the step a2), the "layering the mixture" is achieved via centrifugation, and the parameters of the centrifugation may be: 18000~22000 g, 3~7 min. In the step a2), the "layering the mixture" is achieved via centrifugation, and the parameters of the centrifugation may particularly be: 20000 g, 5 min.

In the step a3), the "layering the mixture" is achieved via centrifugation, and the parameters of the centrifugation may be: 800~1200 g, 3~7 min. In the step a3), the "layering the mixture" is achieved via centrifugation, and the parameters of the centrifugation may particularly be: 1000 g, 5 min.

The phospholipids vortexed in step a1 may be one or more of b1), b2) or b3):

b1) 1,2-di-(9Z-octadecenoyl)-sn-glycero-3-phosphocholine (DOPC);

b2) 1,2-di-(9Z-octadecenoyl)-sn-glycero-3-phosphocholine (DOPC) and 1,2-di-(9Z-octadecenoyl)-sn-glycero-3-phosphoethanolamine (DOPE);

b3) 1,2-di-(9Z-octadecenoyl)-sn-glycero-3-phosphocholine (DOPC) and 1,2-di-octadecanoyl-sn-glycero-3-phosphocholine (DSPC).

The neutral lipid vortexed in step a1 may be one or more of c1) or c2): c1) triacylglycerol; c2) cholesteryl oleate (CO) and triacylglycerol.

In the b2), the mass ratio of 1,2-di-(9Z-octadecenoyl)-sn-glycero-3-phosphocholine and 1,2-di-(9Z-octadecenoyl)-sn-glycero-3-phosphoethanolamine may be 1:0.01~2;

In the b3), the mass ratio of 1,2-di-(9Z-octadecenoyl)-sn-glycero-3-phosphocholine and 1,2-di-octadecanoyl-sn-glycero-3-phosphocholine may be 1:0.01~2; and in c2), the mass ratio of triacylglycerol and cholesteryl oleate may be 1~5:1. In the b2), the mass ratio of 1,2-di-(9Z-octadecenoyl)-sn-glycero-3-phosphocholine and 1,2-di-(9Z-octadecenoyl)-sn-glycero-3-phosphoethanolamine may particularly be 2:1, 1:1 or 1:2; in the b3), the mass ratio of 1,2-di-(9Z-octadecenoyl)-sn-glycero-3-phosphocholine and 1,2-di-octadecanoyl-sn-glycero-3-phosphocholine may particularly be 2:1, 1:1 or 1:2; and in the c2), the mass ratio of triacylglycerol and cholesteryl oleate may particularly be 5:1, 4:1, 3:1 or 2:1.

The preparation method of triacylglycerol (TAG) is as follows: (1) taking one dead SD rat, and taking and mincing its subcutaneous fat and omentum majus fat; (2) placing the minced tissue obtained from step (1) into a centrifugal tube, and adding fat extraction liquid A (chloroform:deionized water=1:1, v/v) and intensely vortexing for 1 min, and then centrifuging at 8000 g for 10 min; (3) taking the lower organic phase obtained in the step (2) to place into a new centrifugal tube, if it is found that the organic phase is turbid, the organic phase is repeatedly extracted according to the extraction process in the step (2), until it is clear; (4) taking the lower organic phase obtained in the step (3) and blow-drying under highly pure nitrogen (if it is found that the lower organic phase becomes turbid, the lower organic phase is repeatedly extracted according to the extraction process in the step (2)); and (5) taking the lower organic phase obtained in the step (4) and blow-drying under highly pure nitrogen (no change in weighting for 3 consecutive times), and the resulting product is triacylglycerol.

The triacylglycerol may be glycerol triolein (TO). The glycerol triolein (TO) is particularly a product from Millipore-Sigma (St. Louis, Mo.), with the product item: 92860.

The mass ratio of the phospholipid and neutral lipid may be any one of (d1) to (d6): (d1) 0.25~3:5; (d2) 3:5; (d3) 2:5; (d4) 1:5; (d5) 1:10; (d6) 1:20.

The adiposomes prepared by the above preparation method of adiposomes also fall into the protection scope of the present invention.

The present invention also provides a method for preparing artificial lipid droplets.

The method for preparing artificial lipid droplets provided by the present invention comprises recruiting one or more resident proteins and/or functional proteins on the adiposomes prepared according to any one of the above preparation methods of adiposomes, to obtain the artificial lipid droplets.

The resident proteins may be MLDS proteins, MDT-28 proteins or Perilipin-2 proteins. The functional proteins may be adipose triacylglycerol lipase (ATGL). The MLDS proteins may be the following e1) or e2): e1) proteins, the amino acid sequence of which is shown as SEQ ID NO: 2 in the Sequence Listing; e2) proteins having the same function as MLDS proteins, which are obtained by substituting and/or deleting and/or adding one to ten amino acid residues on the proteins shown in e1). The MDT-28 proteins may be the following f1) or f2): f1) proteins, the amino acid sequence of which is shown as SEQ ID NO: 4 in the Sequence Listing; 2) proteins having the same function as MDT-28 proteins, which are obtained by substituting and/or deleting and/or adding one to ten amino acid residues on the proteins shown in f1). The Perilipin-2 proteins may be the following g1) or g2): g1) proteins, the amino acid sequence of which is shown as SEQ ID NO: 6 in the Sequence Listing; g2) proteins having the same function as Perilipin-2 proteins, which are obtained by substituting and/or deleting and/or adding one to ten amino acid residues on the proteins shown in g1). The ATGL may be the following h1) or h2): h1) proteins, the amino acid sequence of which is shown as SEQ ID NO: 8 in the Sequence Listing; h2) proteins having the same function as ATGL, which are obtained by substituting and/or deleting and/or adding one to ten amino acid residues on the proteins shown in h1).

The artificial lipid droplets prepared by the above method for preparing artificial lipid droplets also fall into the protection scope of the present invention.

The present invention also provides a method for preparing artificial lipoproteins.

The method for preparing artificial lipoproteins provided by the present invention comprises recruiting one or more apolipoproteins on the adiposomes prepared according to any one of the above preparation methods of adiposomes, to obtain artificial lipoproteins.

The apolipoproteins may be Apo A-I.

The Apo A-I may be obtained by specifically referring to the process recorded in the literature: Peitsch, M. C. et al., A purification method for apolipoprotein A-I and A-II. Anal Biochem 178, 301-305 (1989), which is incorporated by reference herein in its entirety.

The artificial lipoproteins prepared by the above method for preparing artificial lipoproteins also fall into the protection scope of the present invention.

Any one of (j1) to (j6) also falls into the protection scope of the present invention: (j1) use of adiposomes prepared by any one of the above preparation methods of adiposomes in the manufacture of artificial lipid droplets and/or artificial lipoproteins and/or drug carriers; (j2) use of artificial lipid droplets prepared by any one of the above preparation methods of artificial lipid droplets in the manufacture of drug carriers; (j3) use of artificial lipid droplets prepared by any one of the above preparation methods of artificial lipid droplets in the manufacture of drugs; (j4) use of artificial lipoproteins prepared by any one of the above preparation methods of artificial lipoproteins in the manufacture of drug carriers; (j5) use of artificial lipoproteins prepared by any one of the above preparation methods of artificial lipoproteins in the manufacture of drugs; (j6) use of adiposomes prepared by any one of the above preparation methods of adiposomes as drug carriers.

To address the above technical problems, the present invention also provides a drug.

The active components of the drug provided by the present invention are adiposomes loaded with compounds having medicinal functions; and the adiposomes are the adiposomes prepared by any one of the above preparation method of adiposomes. The drug may be a fat-soluble drug. The fat-soluble drug may be a drug which is intersoluble with neutral lipids. The neutral lipids may particularly be triacylglycerol. The drug may particularly be a drug or a drug candidate which can treat Type II diabetes and/or metabolic disorders. In the above drug, the compound having medicinal functions may be the compound shown as formula a;

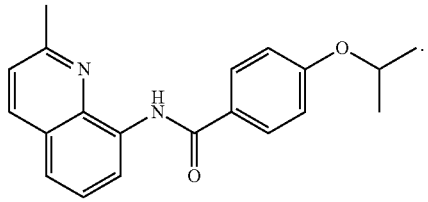

Formula a

In the above drug, the compound having medicinal functions may particularly be CDN 1163 produced by TOCRIS Bioscience (Bristol, UK), with the product item: 5869. The "adiposomes loaded with a compound having medicinal functions" are the drug-loaded adiposomes in Example 3.

The preparation method of drug-loaded adiposomes is particularly as follows: (1) taking 10 mg TAG into a micro-centrifugal tube, and adding 100 μl chloroform for sufficient dissolution to obtain a TAG solution; (2) taking 2 mg CDN 1163 into another micro-centrifugal tube, and adding 200 μl chloroform for sufficient dissolution to obtain a drug solution with a concentration of 10 μg/μl; (3) after the steps (1) and (2) are completed, uniformly mixing the TAG solution and the drug solution, and then blow-drying the solvent with highly pure nitrogen, to obtain a mixed substance; (4) taking 80 μL DOPC solution (containing 2 mg DOPC therein) into a new micro-centrifugal tube, and blow-drying the solvent with highly pure nitrogen; (5) adding 100 μL buffer B and 6 mg mixed substance obtained in the step (3) into the micro-centrifugal tube in which the step (4) has been completed, vortexing for 4 min (vortexing 10 s, pausing 10 s), to obtain a milky lipid mixture A, and then centrifuging the milky lipid mixture A at 20000 g for 5 min; after centrifuged, the precipitate fraction A is at the bottom of the micro-centrifugal tube, and the liquid phase system presents two layers (the upper layer is white band A, and the portion below the white band A is solution A); (6) after the step (5) is completed, removing the solution A and the precipitate fraction A by the means of drawing, and keeping the white band A, adding 100 μl buffer B, vortexing, to obtain a milky lipid mixture B, and centrifuging the lipid mixture B at 20000 g for 5 min; after centrifuged, if there are precipitates at the bottom of the micro-centrifugal tube, the precipitates are the precipitate fraction B, and the liquid phase system presents two layers (the upper layer is white band B, and the portion below the white band B is solution B); (7) after the step (6) is completed, removing the solution B and the precipitate fraction B by the means of drawing, and keeping the white band B, adding 100 μl buffer B, vortexing, to obtain a milky lipid mixture C, and centrifuging the lipid mixture C at 20000 g for 5 min; after centrifuged, the liquid phase system presents two layers (the upper layer is white band C, and the portion below the white band C is solution C). The step (7) is the repeat of the step (6), and in the practical use, the number of repeating the step (6) is controlled based on that there is no precipitate in the layer under the white band. (8) After the step (7) is completed, taking the white band C, adding 100 μl buffer B, uniformly vortexing, and centrifuging at 1000 g for 5 min; after centrifuged, the liquid phase system presents two layers (the upper layer is white band D, and the portion below the white band D is solution D). The solution D is collected, which is the drug-loaded adiposome.

The present invention provides a preparation method of adiposomes and use thereof. One preparation method of adiposomes provided by the invention makes adiposomes consisting of a neutral lipid core and a monolayer phospholipid membrane by vortexing neutral lipid and phospholipid and using a two-step process for purification. The artificial lipid droplets are obtained by recruiting resident proteins and/or functional proteins, such as bacterial proteins MLDS, nematoid proteins MDT-28, mammalian proteins Perilipin-2, adipose triacylglycerol lipase (ATGL) on the adiposomes; the artificial lipoproteins are obtained by recruiting apolipoproteins, such as Apo A-I (apolipoprotein A-I) on the adiposomes. The adiposomes, artificial lipid droplets and artificial lipoproteins prepared by the preparation method provided by the present invention can be used as drug carriers, thereby to complete various biological and medical goals.

THE DESCRIPTION OF DRAWINGS

FIG. 1 is an illustration of preparing and purifying adiposomes by using vortexing and two-step centrifugation. A: A flowchart of preparing adiposomes: a: the components for preparing adiposomes; b: a flowchart of preparing adiposomes, in which the blue arrow represents vortexing and red arrow represents the removed fractions. B: The morphologies of various fractions in the preparation process of adiposomes: a: observed results under an optical microscope (scale=10 μm), in which the arrows represent non-spherical structures, the left image is the original preparation fraction, the middle image is the precipitate fractions and the right image is the upper fraction; b: observed results under a fluorescence microscope (scale=10 μm), in which the arrows represent non-spherical structures, the left image is the original preparation fraction, the middle image is the precipitate fractions and the right image is the upper fraction; c: the results of positive staining by a transmission electron microscope (scale=1 μm), in which the left image is the original preparation fraction, the middle image is the precipitate fractions and the right image is the upper fraction. C: The morphologies of adiposomes observed under an optical microscope (scale=10 μm), in which the left image is obtained with a differential interference phase contrast optical microscope, and the right image is obtained with a fluorescence microscope. D: The results of positive staining adiposomes and liposomes by a transmission electron microscope (scale=500 nm), in which the left image shows adiposomes, and the right image shows liposomes.

FIG. 2 is the characteristics of adiposomes. A: The morphologies of adiposomes and mitochondria (scale=500 nm), a: the observed results by a transmission electron microscope, in which the left image shows adiposomes, and the right image shows mitochondria; b: the observed results by a cryoelectron microscope, in which the left image shows adiposomes, and the right image shows mitochondria. B: The diagram of sizes of adiposomes measured through dynamic light scattering (DLS), polydispersity index=0.085. C: The graph of DOPC/total lipids ratio of fractions analyzed by thin layer chromatography in the process of adiposomes preparation: a: the results of staining samples with iodine vapor (lane 1: lipid Marker, lane 2: the original preparation fraction, lane 3: the mixed fractions, and lane 4: adiposome a); b: the DOPC/total lipids ratio of fractions, N=3, means±variance. D: The morphologies of adiposomes and lipid droplets: a: the morphology of adiposomes, in which the left image is the result by visual observations, the middle image is the observed result under an optical microscope, and the right image is the observed result under a fluorescence microscope; b: the morphology of mice liver tissue-lipid droplets, in which the left image is the result by visual observations, the middle image is the observed result under an optical microscope, and the right image is the observed result under a fluorescence microscope; c: the morphology of mice brown adipose tissue—lipid droplets, in which the left image is the result by visual observations, the middle image is the observed result under an optical microscope, and the right image is the observed result under a fluorescence microscope; and d: the morphology of *Rhodococcus* sp. RHA1-lipid droplets, in which the left image is the result by visual observations, the middle image is the observed result under an optical microscope, and the right image is the observed result under a fluorescence microscope.

FIG. 3 is the influence of various factors on adiposomes preparation. A: The influence of different vortex time on adiposomes (1: adiposome b, 2: adiposome c, 3: adiposome d, and 4: adiposome a): a: the morphology of adiposomes, b: the optical density of adiposomes, c: the size of adiposomes; B: the optical density (a) and size (b) of adiposomes prepared with different ratios of DOPC and TAG; C: the optical density (a) and size (b) of adiposomes prepared with different ratios of DOPC and DSPC; D: the optical density (a) and size (b) of adiposomes prepared with different ratios of DOPC and DOPE; E: the optical density (a) and size (b) of adiposomes prepared with different ratios of TAG and CO; and F: the optical density (a) and size (b) of adiposomes incubated for 7 days at 4° C. or room-temperature.

FIG. 4 is a set of the microscopic images of adiposomes stored for 7 days at room-temperature or 4° C. (scale=10 μm). A and C are under an optical microscope; B and D are under a fluorescence microscope.

FIG. 5 is the isolation and purification of SMT3-Perilipin-2 proteins. A: Analysis of whole cell lysates before and after IPTG induction by SDS-PAGE isolation and through silver staining (top image) and Western-blot (bottom image). Black arrow indicates a band to which SMT3-Perilipin-2 proteins correspond; B: The analysis results of SDS-PAGE and colloidal blue staining of various fractions purified by a nickel ion metal affinity chromatography column; C: Further purification of SMT3-Perilipin-2 proteins eluted from the nickel column by molecular sieves, four fractions (1, 2, 3 and 4) are collected according to their retention volumes, respectively, and they are separated with blue short lines in this figure; and D: SDS-PAGE analysis of SMT3-Perilipin-2 proteins purified with a nickel column (imidazole elution) and the fractions obtained through molecular sieves.

FIG. 6 is that the artificially recombinant lipid droplet resident/structural proteins of different specie sources are recruited onto adiposomes.

FIG. 7 is the artificial lipid droplets are constructed by recruiting lipid droplet resident/structural proteins. A: The schematic views of artificial lipid droplet construction; B: Adiposomes may recruit lipid droplet resident/structural proteins-GFP fusion proteins; and C: Measurement of saturation degree of SMT3-Perilipin-2 proteins.

Figure 10:
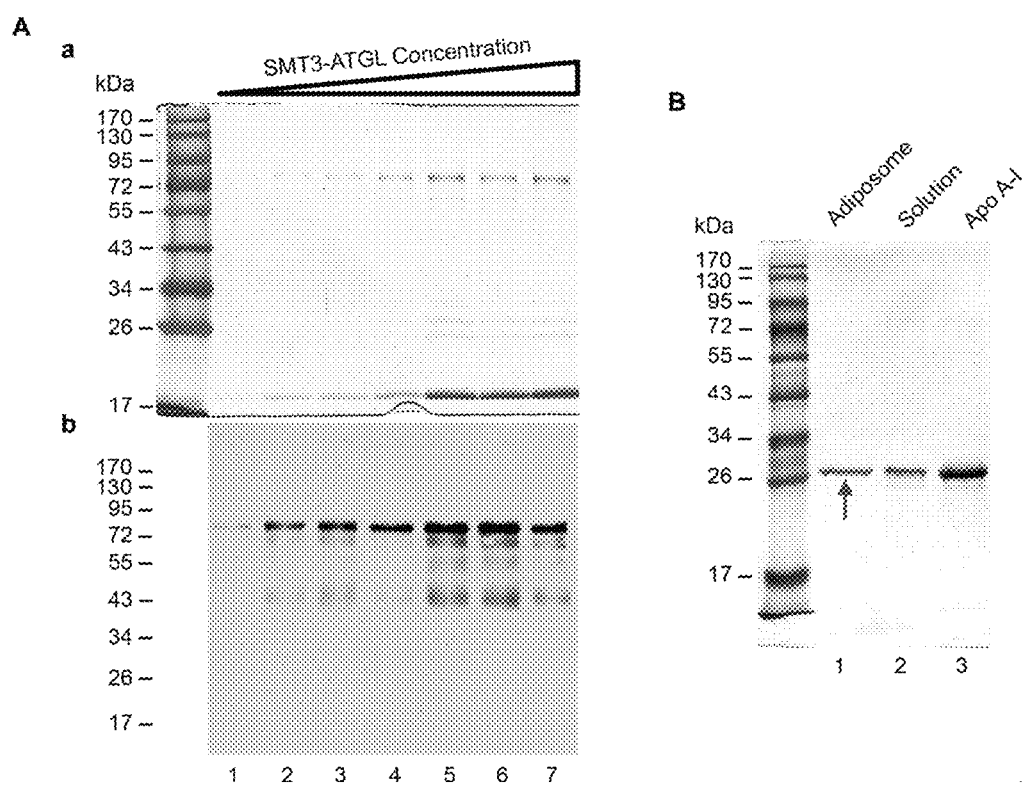

FIG. 10 is that ATGL and Apo A-I are recruited on adiposomes. A: Measurement of saturation degree of SMT3-ATGL proteins, in which the added concentrations of SMT3-ATGL proteins to which lanes 1 to 7 correspond are: 0.091, 0.132, 0.171, 0.209, 0.244, 0.278, and 0.310 μg/μL, respectively; and B: artificial lipoproteins are constructed by recruiting apolipoproteins, Apo A-I, of high density lipoproteins.

Figure 11:
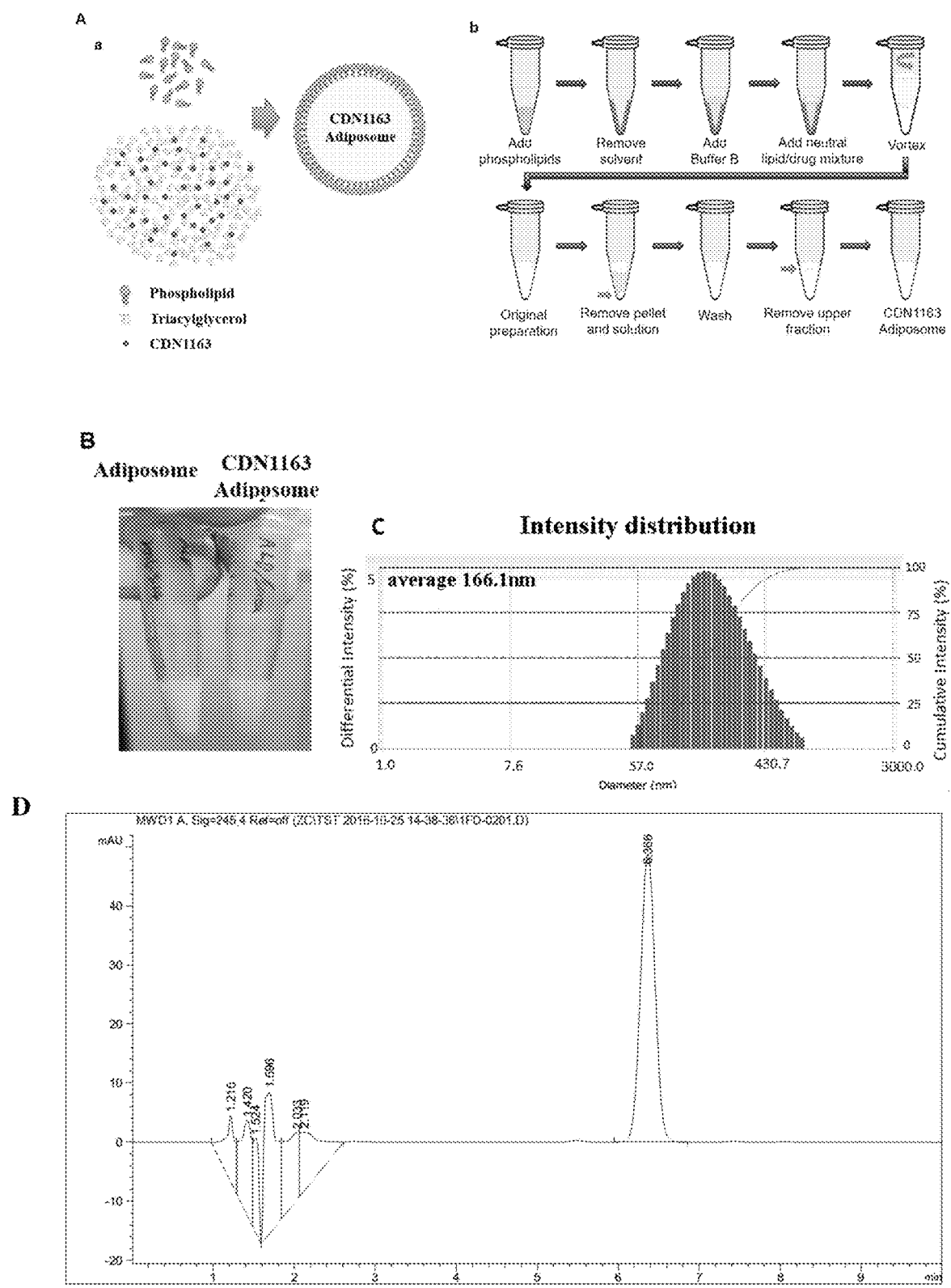

FIG. 11 is an illustration of preparing drug-loaded adiposomes using vortexing and two-step centrifugation. A: the flowchart of preparing drug-loaded adiposomes, a is the components for preparing drug-loaded adiposomes; b is the flowchart of preparing drug-loaded adiposomes; B: The prepared drug-loaded adiposomes; C: The size of drug-loaded adiposomes measured by dynamic light scattering (DLS); and D: The detection result of high performance liquid chromatography.

THE BEST MODE OF EMBODIMENTS

The detailed description would be further made in combination with the following specific embodiments, and the given examples are only intended to illustrate the present invention, not to limit the scope of the present invention.

The experimental processes in the following examples, unless specifically indicated otherwise, are all the conventional process.

The materials, reagents and the like used in the following examples, unless specifically indicated otherwise, are all commercially available.

The term "adiposome", as used herein, is defined as a class of artificially synthesized structure which takes natural or artificially synthesized neutral lipids as core and is packaged with natural or artificial synthesized polar lipid monolayer membrane. The lipid composition and the morphology of adiposomes are similar as those of lipid droplets, and thus adiposomes can be used as the main raw materials for preparing artificial lipid droplets.

1,2-di-(9Z-octadecenoyl)-sn-glycero-3-phosphocholine (DOPC) is a product from Avanti Polar Lipids (Alabaster, Ala.), in a state of DOPC solution, that is, DOPC is dissolved into chloroform. 1,2-di-(9Z-octadecenoyl)-sn-glycero-3-phosphoethanolamine (DOPE) is a product from Avanti, in a state of DOPE solution, that is, DOPE is dissolved into chloroform. 1,2-di-octadecanoyl-sn-glycero-3-phosphocholine (DSPC) is a product from Avanti Polar Lipids, in a state of DSPC solution, that is, DSPC is dissolved into chloroform. Cholesteryl oleate (CO) is a product from Alfa Aesar (Haverhill, Mass.). Nile red is a product from Sigma-Aldrich (St. Louis, Mo.). LipidTOX red is a product from Invitrogen (Carlsbad, Calif.), with the product item: H34476. Anti-Perilipin-2 is a product from Abcam (Cambridge, UK), with the product item: ab108323. Percoll is a product from GE Healthcare (Chicago, Ill.). Uranyl acetate, 25% glutaraldehyde and EMbed 812 embedding kit are all products from Electron Microscopy Sciences (Hatfield, Pa., USA). Osmium tetraoxide (EM grade) is a product from NAKALAI Tesque (Kyoto, Japan). Tannic acid is a product from Sigma. C57BL/6 mice are products from Beijing Vital River Laboratories. Dynamic light scatter (DLS, Delsa Nano C Particle Analyzer, Beckman Coulter, Brea, Calif.).

The "vortexing" in the following examples are all preformed using Vortex-Genie 1 Touch Mixer (Scientific Industries, Inc., Bohemia, N.Y., USA), and "colloidal blue staining" is performed using Colloidal Blue staining Kit (a product from Invitrogen, with the product item: LC6025).

Mitochondria is obtained by isolating brown adipose tissue of C57BL/6 mouse, and the specific isolating method refers to Yu, J. et al. Lipid droplet remodeling and interaction with mitochondria in mouse brown adipose tissue during cold treatment. Biochim Biophys Acta 1853, 918-928, doi:10.1016/j.bbamcr.2015.01.020(2015), the content of which is incorporated by reference herein in its entirety.

The method for preparing 2.5% glutaraldehyde solution comprises: dissolving 25% glutaraldehyde into 0.1M PB buffer with a pH of 7.4, such that the mass concentration of glutaraldehyde in the system is 2.5%.

The method for preparing triacylglycerol (TAG) in Example 1 is as follows: (1) taking one dead SD rat, and taking and mincing its subcutaneous fat and omentum majus fat; (2) placing the minced tissue obtained from (1) into a centrifugal tube, and adding fat extraction liquid A (chloroform:deionized water=1:1, v/v) and intensely vortexing for 1 min, then centrifuging at 8000 g for 10 min; (3) taking the lower organic phase obtained in the step (2) to place into a new centrifugal tube, if it is found that the organic phase is turbid, the organic phase is repeatedly extracted according to the extraction process in the step (2), until it is clear; (4) taking the lower organic phase obtained in the step (3) and blow-drying under highly pure nitrogen (if it is found that the lower organic phase becomes turbid, the lower organic phase is repeatedly extracted according to the extraction process in the step (2)); and (5) taking the lower organic phase obtained in the step (4) and blow-drying under highly pure nitrogen (no change in weighing for 3 consecutive times), and the product is triacylglycerol.

The solutes of the buffer B and their concentrations in the buffer are: 20 mM HEPES (15 mM-25 mM HEPES are all feasible in practical use), 100 mM KCl (80 mM-120 mM KCl are all feasible in practical use), 2 mM $MgCl_2$ (1.5-2.5 mM $MgCl_2$ are all feasible in practical use); the solvent is deionized water; and pH is 7.4 (7.2-7.6 are all feasible in practical use).

Liposomes are unilamellar liposomes prepared by mixing Phosphatidylcholine and Phosphatidylethanolamine in a mass ratio of 3:7, and then using a mini-extruder set with 100 nm polycarbonate filters (Avanti Biosciences, Stony Brook, N.Y.), and see Nakatogawa, H., Ichimura, Y. & Ohsumi, Y. Atg8, a ubiquitin-like protein required for autophagosome formation, mediates membrane tethering and hemifusion. Cell 130, 165-178, doi:10.1016/j.cell.2007.05.021 (2007) for the specific preparation method, the contents of which are herein incorporated in their entirety.

Adiposomes or lipid droplets are observed using a fluorescence microscope, and the specific steps are as follows: adiposomes or lipid droplets are stained with Nile red (concentration: 1 µg/ml) or LipidTOX red diluent (LipidTOX red is diluted with buffer B in a ratio of 1:1000 to produce LipidTOX red diluent), and incubated at room-temperature for 30 min, a 6 µl of incubated adiposomes or lipid droplets is dropped to a slide and then mixed with 2 µl Antifade mounting medium (Beyotime, with the product item: P0126) and covered by a coverslip. Fluorescence images are captured using Zeiss Axio Imager M2 fluorescence microscope (Zeiss, Oberkochen, Germany), Olympus FV1000 fluorescence confocal microscope (GE Healthcare, Chicago, Ill.), or DeltaVision OMX V3 super-resolution microscope (Olympus, Centerville, Pa.).

The specific steps of positive staining in transmission electron microscope are as follows: 8 µl of adiposomes or liposomes are taken to drop onto a glow-discharged copper grid coated with a carbon film, resting for 1 min, followed by blotting with filter paper to remove extra sample; then the sample is fixed with 1% osmium tetroxide for 10 min, and rinsed with deionized water; then the sample is stained with 0.1 tannic acid for 5 min and 2% uranyl acetate for 5 min successively, and is rinsed with deionized water. Micrographs are captured using Tecnai Spirit (FEI) transmission electron microscope at 100 kV (Thermo Fischer, Waltham, Mass.).

Adiposomes or mitochondrias are observed using transmission electron microscope, and the specific steps are as follows: adiposomes or mitochondria are quickly mixed with melted 3% agarose having a low melting point, and solidified on ice and cut into blocks of approximately 1 mm3. The blocks are fixed with 2.5% glutaraldehyde for 30 min, and subsequently are fixed with 1% osmium tetroxide in 0.1 M PB buffer (pH 7.4) for 1 h at room temperature, to give fixed blocks. The fixed blocks are washed with deionized water, dehydrated with ethanol, and then infiltrated and embedded with EMbed 812 embedding kit (Electron Microscopy Sciences), and are polymerized at 60° C. for 24 h. 70 nm of ultrathin sections are prepared using Leica EM UC6 Ultramicrotome (Leica Microsystems, Buffalo Grove, Ill.). Micrographs are captured using Tecnai Spirit (FEI) transmission electron microscope at 100 kV.

Adiposomes or mitochondrias are observed using cryo-electron microscope, and the specific steps are as follows: 4 µl of adiposomes or mitochondrias are dropped onto a copper grid, and blotted for 3 seconds in 100% humidity using Vitrobot Mark IV (the product of FEI) and then vitrified by quickly plunging into liquid ethane pre-cooled with liquid nitrogen. Micrographs are captured using Titan Krios cryo-electron microscope equipped with Gatan Ultra-Scan4000 Camera (Product number: 895) (the product of FEI) at 300 kV (Gatan, Pleasantville, Calif.).

Buffer T is a buffer containing 50 mM Tris-HCl and 150 mM NaCl with a pH of 7.4.

Vector pET28a is a product of Novagen (Madison, Wis.). Vector pGEX-6p-1 is purchased from Novagen. Nickel ion metal affinity chromatography column fillers are Chelating Sepharose Fast Flow chelated with nickel ions, which are products of Amersham Biosciences (Little Chalfont, UK). GST affinity chromatography column fillers are products of Sangon Biotech (Shanghai) Co., Ltd.

"Modified pET28a plasmid" is recorded in the following literature: Hu, W., Wu, H., Zhang, H., Gong, W. & Perrett, S. Resonance assignments for the substrate binding domain of Hsp70 chaperone Ssa1 from *Saccharomyces cerevisiae*. Biomol NMR Assign 9, 329-332, doi:10.1007/s12104-015-9603-5 (2015). "Modified pET28a plasmid" is referred to as hereinafter vector pET28a-SMT3.

Example 1: Preparation of Adiposomes

I. Preparation of Adiposome A

1, Adiposome a was prepared using vortexing and two-step centrifugation, and the specific steps were as follows:

80 µL of DOPC solution (2 mg of DOPC were contained herein) was added into a micro-centrifugal tube, and the solvent was blow-dried with highly pure nitrogen.

After the step (1) was completed, 100 μl buffer B and 5 mg TAG were added to the micro-centrifugal tube, vortexing for 4 min (vortexing 10 s, pausing 10 s), to give milky lipid mixture 1 (i.e., original preparation fraction), and the lipid mixture 1 was centrifuged at 20000 g for 5 min (centrifuging for 3-7 min at 18000-22000 g is feasible in practical use). After centrifugation, the precipitate fraction 1 was at the bottom of the micro-centrifugal tube, and the liquid phase system presented two layers (the upper layer was white band 1, and the portion below the white band 1 was solution 1).

After the step (2) was completed, the solution 1 and the precipitate fraction 1 were removed by the means of drawing, but the white band 1 was kept, 100 μl buffer B was added for vortexing, to obtain a milky lipid mixture 2, and the lipid mixture 2 was centrifuged at 20000 g for 5 min (centrifuging for 3-7 min at 18000-22000 g is feasible in practical use). After centrifugation, if there were precipitates at the bottom of the micro-centrifugal tube, the precipitates were the precipitate fraction 2, and the liquid phase system presented two layers (the upper layer was white band 2, and the portion below the white band 2 was solution 2).

After the step (3) was completed, the solution 2 and the precipitate fraction 2 were removed by the means of drawing, and the white band 2 was kept, 100 μl buffer B was added for vortexing, to obtain a milky lipid mixture 3, and the lipid mixture C was centrifuged at 20000 g for 5 min (centrifuging for 3-7 min at 18000-22000 g is feasible in practical use). After centrifugation, the liquid phase system presented two layers (the upper layer was white band 3, and the portion below the white band 3 was solution 3).

(5) After the step (4) was completed, the white band 3 was taken and added with 100 μl buffer B, for uniformly vortexing, and centrifuged at 1000 g for 5 min (centrifuging for 3-7 min at 800-1200 g is feasible in practical use). After centrifugation, the liquid phase system presented two layers (the upper layer was white band 4, and the portion below the white band 4 was solution 4). The solution 4 was collected, which was the adiposomes a.

(5) After the step (4) was completed, the white band 3 was taken and added with 100 μl buffer B, for uniformly vortexing, and centrifuged at 1000 g for 5 min (centrifuging for 3-7 min at 800-1200 g is feasible in practical use). After centrifuged, the liquid phase system presented two layers (the upper layer was white band 4, and the portion below the white band 4 was solution 4). The solution 4 was collected, which was the adiposomes a.

The white band 4 in the above steps was named as upper fraction. The precipitate fraction 1 and the precipitate fraction 2 in the above steps were mixed and named as precipitate fraction. The precipitate fraction and the upper fraction in the above steps were mixed and named as mixed fraction.

Figure 1:
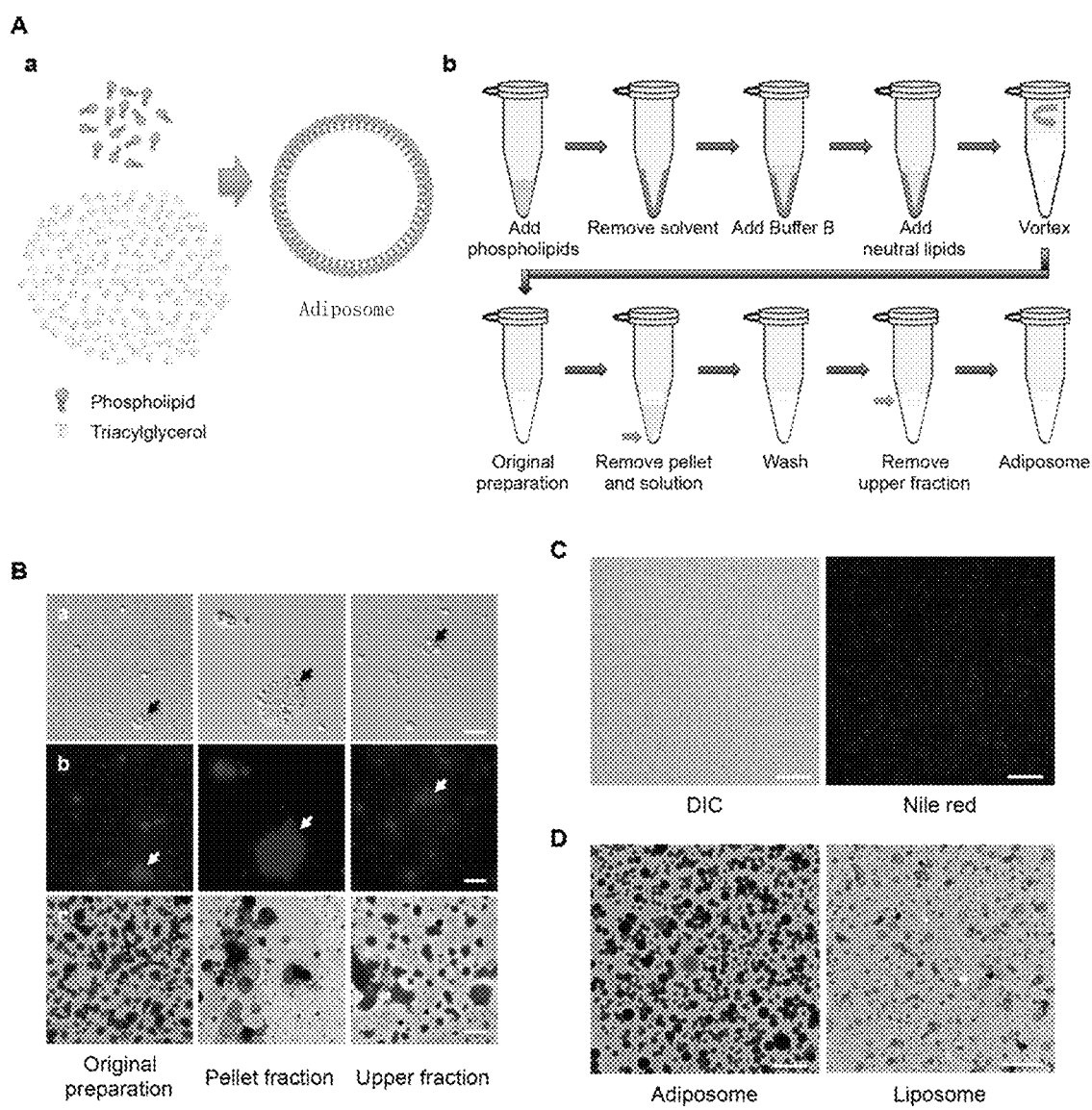

The specific flow of preparing adiposome a using the above method refers to A in FIG. 1 (in which, a was the components for preparing adiposome a, b was the flowchart of preparing adiposome a). The morphologies of various fractions in the process of preparing adiposome a were observed using an optical microscope and a fluorescence microscope, and were transmission electron microscope positive stained using microscope, and the results were as follows: in addition to spherical structures containing neutral lipids in original preparation fraction, precipitate fraction and upper fraction, there were also many other types of structures (B in FIG. 1); all structures of solution 3 were almost spherical, and were Nile red positive, moreover, the sizes of structures labeled with Nile red were consistent with the sizes of spherical structures in optical microscope images, indicating that these spherical structures all contained TAG core (C in FIG. 1); adiposome a and liposomes were transmission electron microscope positive stained using microscope, and the results showed that there were obvious difference between them (D in FIG. 1).

2, Characteristics of Adiposome a

Figure 2:
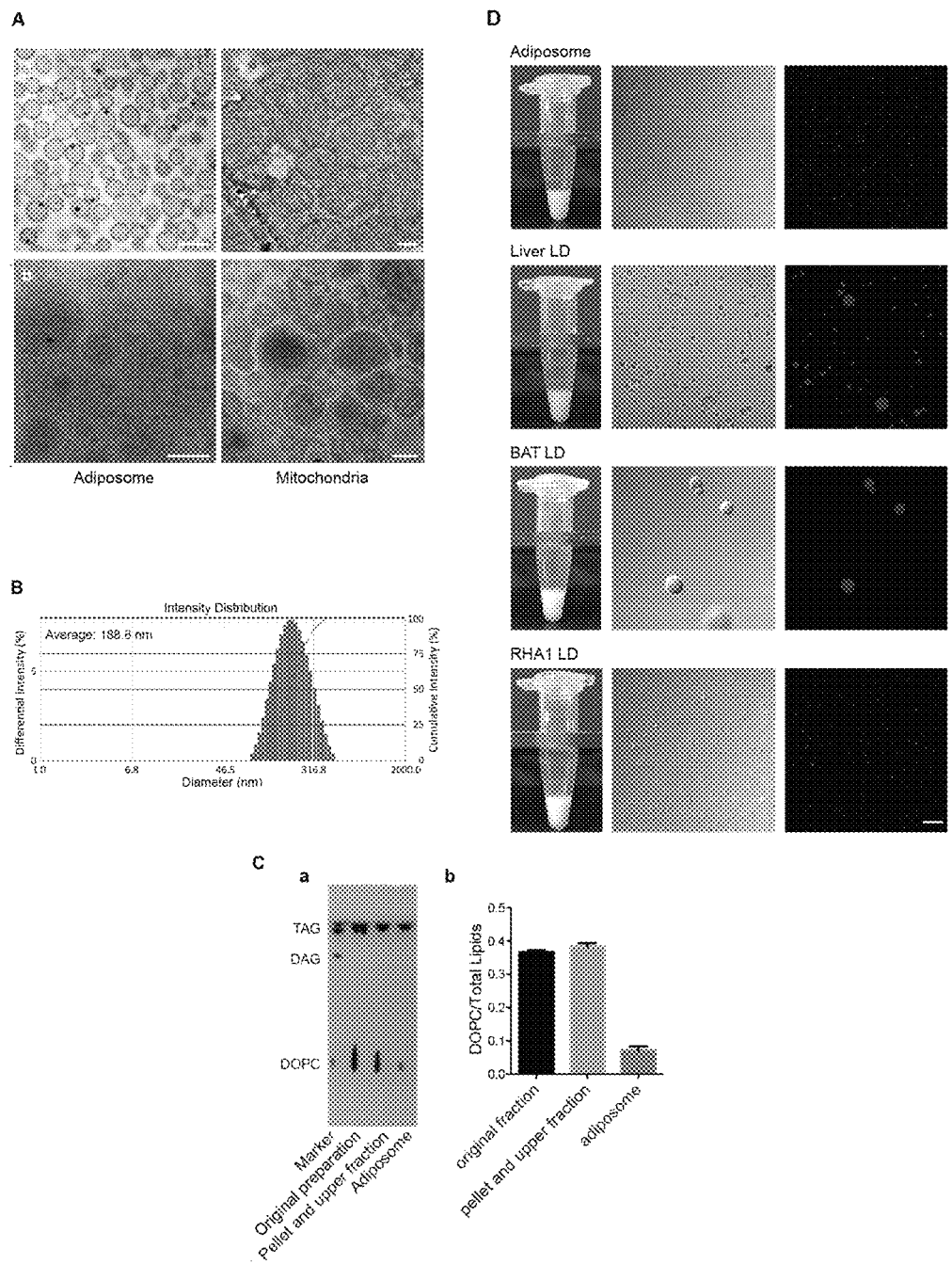

Adiposome a and mitochondria were observed using transmission electron microscope, respectively, adiposome a and mitochondria were observed using cryoelectron microscope, respectively, and the results showed that (A in FIG. 2) adiposome a was packaged with a monolayer phospholipid membrane, and mitochondria was packaged with bilayer phospholipid membrane.

The average size of adiposome a was about 189 nm (B in FIG. 2), as measured using dynamic light scatter, and the volume ratio of DOPC to total lipids (total lipids were TAG and DOPC) in adiposome a was calculated as 6.6% using the equation in literature (Ding Y, Zhang S, et al. Isolating lipid droplets from multiple species. Nat Protoc. 2013 January; 8(1): 43-51.doi:10.1038/nprot.2012.142.Epub 2012 Dec. 6.).

Lipids were analyzed using thin layer chromatography, and the specific steps were as follows:

a, materials to be extracted were taken (the sum of the volume of materials to be extracted and the volume of buffer B in the following fat extraction liquid B was 300 μl), and extracted using fat extraction liquid B (consisting of 3000 chloroform, 3000 methanol and buffer B) to obtain lipids (the organic phase was collected and named as organic phase A), the remaining portion was again added with 300 μl chloroform for extraction to further obtain lipids (the organic phase was collected and named as organic phase B); organic phase A and organic phase B were mixed and blow dried with nitrogen to obtain total lipids in the materials to be extracted; the materials to be extracted were adiposome a, lipid mixture 1 (i.e., original preparation fraction) or mixed fraction.

b, the total lipids obtained in step a were dissolved in 100 μl chloroform, and 10 μl solution was loaded to silica gel plate;

c, after the step b was completed, the samples were developed in a developing agent of n-hexane: diethyl ether: glacial acetic acid (volume ratio of 80:20:1) to separate TAG;

d, after the step c was completed, the organic solvents (i.e., n-hexane, diethyl ether, and glacial acetic acid in step c) were volatilized in air, and the silica gel plate was again developed in a solvent system of chloroform:methanol: glacial acetic acid:water (volume ratio of 75:13:9:3), to separate DOPC;

e, after the step d was completed, the samples were stained using saturate iodine vapor and quantified on gray scale of lipid spots with ImageJ software.

The results (C in FIG. 2) showed that the ratio of DOPC and lipids in samples was 7.1±1.2%, which was similar to the calculated value in the step (2), indicating that adiposome a had a structure of a monolayer phospholipid membrane.

(4) Lipid droplets were isolated from C57BL/6 mouse liver tissue, C57BL/6 mouse brown adipose tissue and oleaginous bacterium RHA1, respectively, according to the methods recorded in Ding Y, Zhang S, et al. Isolating lipid droplets from multiple species. Nat Protoc. 2013 January; 8(1): 43-51.doi: 10.1038/nprot.2012. 142.Epub 2012 Dec. 6.) and Yu, J. et al. Lipid droplet remodeling and interaction with mitochondria in mouse brown adipose tissue during cold treatment. Biochim Biophys Acta 1853, 918-928, doi: 10.1016/j.bbamcr.2015.01.020 (2015), each of which is incorporated by reference herein in its entirety, which were successively named as liver tissue-lipid droplet (Liver LD), brown adipose tissue-lipid droplet (BAT LD) and RHA1-lipid droplet (RHA1 LD).

All of adiposome a, RHA1 LD, Liver LD and BAT LD presented milky solution. The average sizes of adiposome a, RHA1 LD, Liver LD and BAT LD were measured using dynamic light scatter, and results showed the particle size of BAT LD was the biggest, the average diameter being 1848 nm; the particle size of RHA1 LD was smallest, the average diameter being 493 nm; the average diameter of adiposome a was 189 nm (B in FIG. 2). The above results were substantially consistent with the results obtained by optical microscope (D in FIG. 2). Adiposomes or lipid droplets were observed using fluorescence microscope, and all of adiposome a, RHA1 LD, Liver LD and BAT LD presented spherical structure (D in FIG. 2), indicating that they all contained TAG core.

3, Factors of Affecting the Formation of Adiposomes

To optimize conditions for preparing adiposomes, we systematically varied two major factors of vortex and two-step process in step 1, i.e., vortex time and the ratio of both raw materials (phospholipids and neutral lipids); measured optical density at 600 nm of wavelength ($OD_{600}$) for reflecting adiposome yield; and measured the size of adiposomes by dynamic light scattering meter.

Optimization of Vortex Time

According to the method of above step 1, adiposome b, adiposome c and adiposome d were obtained except that vortexing for 4 min in step (1) was replaced with vortexing for 1 min, vortexing for 2 min, and vortexing for 3 min, respectively, without other changes in other steps, and then the sizes and optical densities of adiposome a, adiposome b, adiposome c and adiposome d were measured, respectively.

Figure 3:
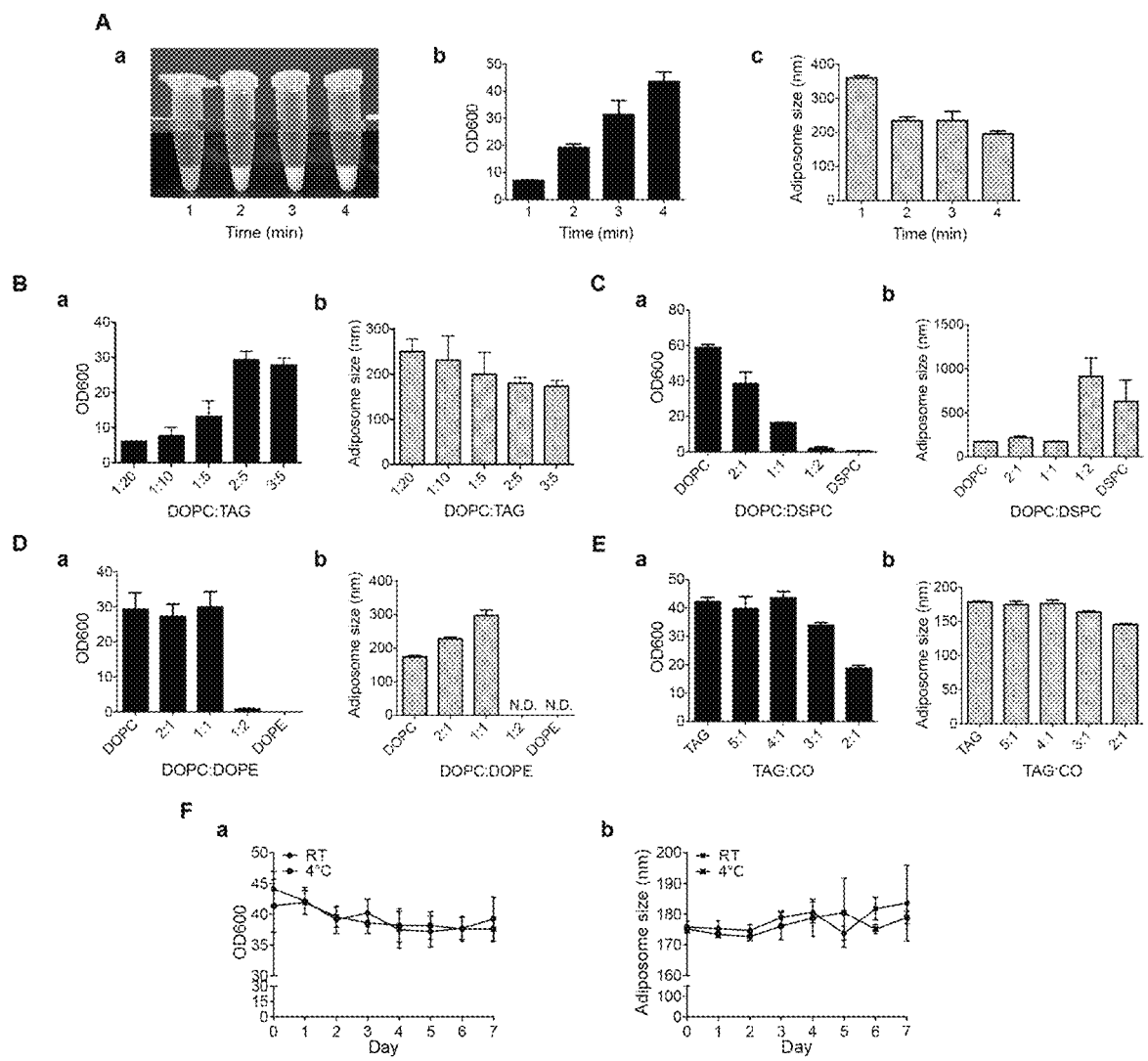

The experimental results were shown in A of FIG. 3. The results indicated that the adiposome yield increased with prolonging of vortex time, while the size of adiposomes decreased with prolonging of vortex time, and reached a minimum value at approximately 2 min and kept a plateau. Combining two factors of higher light density (i.e, higher yield) and larger size of adiposomes, it is determined that the optimum vortex time was 4 min in the step (2) of vortex and two-step process.

(2) Optimization of Phospholipid to Neutral Lipid Ratio

Adiposome a was prepared, in which phospholipid was specifically DOPC, neutral lipid was specifically TAG, and the ratio of DOPC:TAG was 2:5.

According to the method of above step 1, adiposome a1 (the ratio of DOPC:TAG was 1:20), adiposome a2 (the ratio of DOPC:TAG was 1:10), adiposome a3 (the ratio of DOPC:TAG was 1:5) and adiposome a4 (the ratio of DOPC:TAG was 3:5) were obtained except that 2 mg DOPC in step (1) was replaced with 0.25 mg DOPC, 0.5 mg DOPC, 1 mg DOPC and 3 mg DOPC, respectively, without other changes in other steps, and then the sizes and optical densities of adiposome a1, adiposome a2, adiposome a3 and adiposome a4 were measured, respectively.

The experimental results were shown in B of FIG. 3. The results indicated that when the ratio of DOPC and TAG was 2:5, adiposome yield was the highest; the size of adiposomes decreased with an increase in the ratio of DOPC and TAG, reaching a minimum at a DOPC:TAG ratio of 1:5 and kept a plateau. Combining two factors of higher yield and larger size of adiposomes, it is determined that the optimum ratio of DOPC and TAG in preparation of adiposomes was 2:5.

② According to the method of above step 1, adiposome A1 (the ratio of DOPC:DSPC was 2:1), adiposome A2 (the ratio of DOPC:DSPC was 1:1), adiposome A3 (the ratio of DOPC:DSPC was 1:2) and adiposome A4 (phospholipid was only DSPC) were obtained except that 2 mg DOPC in step (1) was replaced with 1.33 mg DOPC and 0.67 mg DSPC, 1 mg DOPC and 1 mg DSPC, 0.67 mg DOPC and 1.33 mg DSPC, and 2 mg DSPC, respectively, without other changes in other steps, and then the sizes and optical densities of adiposome A1, adiposome A2, adiposome A3 and adiposome A4 were measured, respectively.

The results showed that when the ratio of DOPC and DSPC was reduced, that is, the relative content of DSPC increased, adiposome yield significantly decreased (a of C in FIG. 3), but the size of diposomes dramatically increased with decrease in the ratio of DOPC and DSPC (b of C in FIG. 3).

③ According to the method of above step 1, adiposome B1 (the ratio of DOPC:DOPE was 2:1), adiposome B2 (the ratio of DOPC:DOPE was 1:1), adiposome B3 (the ratio of DOPC:DOPE was 1:2) and adiposome B4 (phospholipid was only DOPE) were obtained except that 2 mg DOPC in step (1) was replaced with 1.33 mg DOPC and 0.67 mg DOPE, 1 mg DOPC and 1 mg DOPE, 0.67 mg DOPC and 1.33 mg DOPE, and 2 mg DOPE, respectively, without other changes in other steps, and then the sizes and optical densities of adiposome B 1, adiposome B2, adiposome B3 and adiposome B4 were measured, respectively.

The results showed that the incorporation of DOPE did not affect adiposome yield, and adiposome yield started to dramatically decrease until the ratio of DOPC and DOPE reached 1:2 (a of D in FIG. 3), and the size of adiposomes dramatically increased with decrease in the ratio of DOPC and DOPE, and the size of adiposomes was able to be detected when the ratio of DOPC and DOPE reached 1:2 (b of D in FIG. 3).

④ According to the method of above step 1, adiposome C1 (the ratio of TAG:CO was 5:1), adiposome C2 (the ratio of TAG:CO was 4:1), adiposome C3 (the ratio of TAG:CO was 3:1) and adiposome C4 (the ratio of TAG:CO was 2:1) were obtained except that 5 mg TAG in step (1) was replaced with 4.17 mg TAG and 0.83 mg CO, 4 mg TAG and 1 mg CO, 3.75 mg TAG and 1.25 mg CO, and 3.33 mg TAG and 1.67 mg CO, respectively, without other changes in other steps, and then the sizes and optical densities of adiposome C1, adiposome C2, adiposome C3 and adiposome C4 were measured, respectively.

The results showed that the incorporation of CO did not affect adiposome yield, and not until the ratio of TAG and CO reached 3:1 did the adiposome yield start to dramatically decrease (a of E in FIG. 3), and the size of adiposomes slightly decrease (b of E in FIG. 3), showing the composition of neutral lipids may dramatically affect the yield and size of adiposomes.

4, Stability of Adiposomes

Adiposome a was incubated at room temperature or 4° C. for 7 days. During the incubating procedure, the size and the optical density at $OD_{600}$ of adiposome a were measured daily, and the adiposome was observed under optical microscope and fluorescence microscope.

Figure 4:
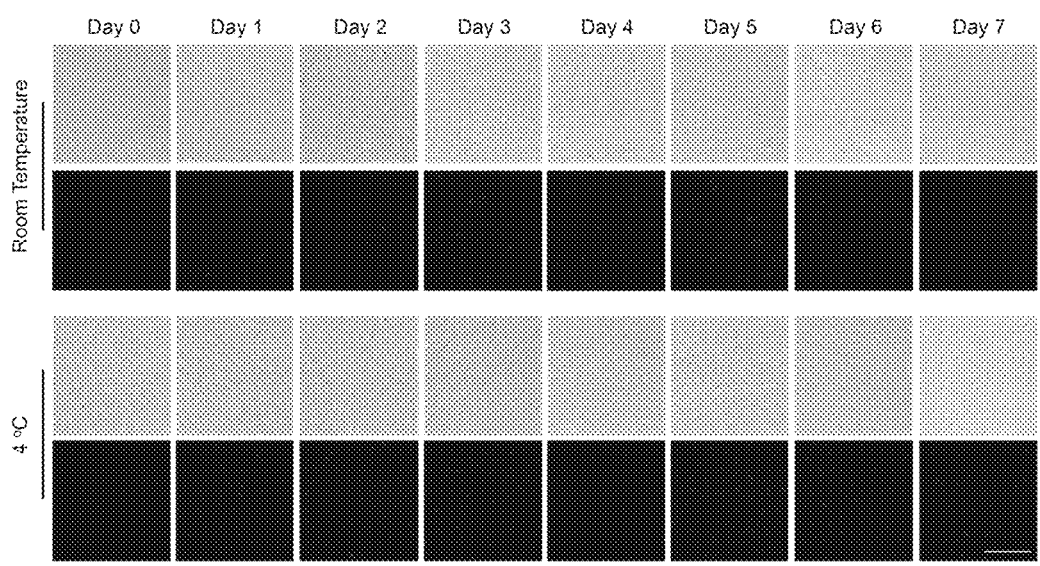

The results (F in FIG. 3 and FIG. 4) showed that during the whole incubating procedure, the optical density and size of adiposome a did not obviously vary. It can be seen that adiposome a was relatively stable.

Example 2, Recombination of Artificial Lipid Droplets by Recruiting Resident Proteins and/or Functional Proteins and Recombination of Artificial Lipoproteins by Recruiting Apolipoproteins Ulp1 in the following Example was recorded in literature: Hu, W., Wu, H., Zhang, H., Gong, W. & Perrett, S. Resonance assignments for the substrate binding domain of Hsp70 chaperone Ssa1 from *Saccharomyces cerevisiae*. Biomol NMR Assign 9, 329-332, doi:10.1007/s12104-015-9603-5 (2015). During the incubating procedure of following experiments, Ulp1 can cleave SMT3 tag on proteins.

Lipid droplets are highly dynamic and are involved in myriad physiological functions and interactions by the mediation of a plurality of lipid droplet proteins. The proteins on lipid droplets can be roughly divided into two categories: resident proteins and dynamic proteins. The resident proteins are thought to be selectively localized on lipid droplets and involved in control of lipid droplet size, and mediate localization of dynamic proteins. For example, phosphorylation of PLIN1 facilitates the location of hormone-sensitive lipase (HSL) on lipid droplets. Therefore, to dissect lipid droplet functions by using adiposomes, it must load lipid droplet resident proteins on adiposomes, and then on the basis that resident proteins were successfully recruited to generate artificial lipid droplets, functional proteins are further recruited. As for lipoproteins, different apolipoproteins are not only specific markers for different lipoproteins, but also one of lipoprotein backbones. In the present invention, lipid droplet resident proteins particularly are lipid droplet resident proteins derived from diverse organisms from bacteria to mammals, including MLDS proteins on RHA1-lipid droplets (RHA1 LD) isolated from oleaginous bacterium RHA1, MDT-28 proteins on nematode lipid droplets and Perilipin-2 proteins in non-adipose cells of mammals, and functional proteins are ATGL. Apolipoproteins particularly are apolipoprotein A1 (apolipoprotein A-I, Apo A-I) from human.

I, Expression and Purification of Proteins

The DNA molecule shown by SEQ ID NO: 1 in artificially synthesized Sequence Listing is MLDS gene, and the protein shown by SEQ ID NO: 2 encoded by DNA molecule shown by SEQ ID NO: 1 is MLDS protein, NCBI number: WP_005261062.1. The DNA molecule shown by SEQ ID NO: 3 in artificially synthesized Sequence Listing is MDT-28 gene, NCBI number: NM_001129054.2, and the protein shown by SEQ ID NO: 4 encoded by DNA molecule shown by SEQ ID NO: 3 is MDT-28 protein, NCBI number: NP_001122526.1. The DNA molecule shown by SEQ ID NO: 5 in artificially synthesized Sequence Listing is Perilipin-2 gene, and the protein shown by SEQ ID NO: 6 encoded by DNA molecule shown by SEQ ID NO: 5 is Perilipin-2 protein, NCBI number: NP_001113.2. The DNA molecule shown by SEQ ID NO: 7 in artificially synthesized Sequence Listing is ATGL gene, and the protein shown by SEQ ID NO: 8 encoded by DNA molecule shown by SEQ ID NO: 7 is ATGL, NCBI number: NP_065109.1. The DNA molecule shown by SEQ ID NO: 9 in artificially synthesized Sequence Listing is MLDS-GFP fusion gene, and the protein shown by SEQ ID NO: 10 encoded by DNA molecule shown by SEQ ID NO: 9 is MLDS-GFP fusion protein. The DNA molecule shown by SEQ ID NO: 11 in artificially synthesized Sequence Listing is MDT-28-GFP fusion gene, and the protein shown by SEQ ID NO: 12 encoded by DNA molecule shown by SEQ ID NO: 11 is MDT-28-GFP fusion protein. The DNA molecule shown by SEQ ID NO: 13 in artificially synthesized Sequence Listing is Perilipin-2-GFP fusion gene, and the protein shown by SEQ ID NO: 14 encoded by DNA molecule shown by SEQ ID NO: 13 is Perilipin-2-GFP fusion protein. Bovine serum albumin is purchased from Sigma, the product item: A4612.

1, Expression and Purification of SMT3-Perilipin-2 Proteins

The fragment between sequences recognized by the restriction enzymes (EcoRI and XhoI) of vector pET28a-SMT3 was replaced with the DNA molecule shown by SEQ ID NO: 5 in Sequence Listing (vector pET28a-SMT3 was cleaved into a large fragment and a small fragment with restriction endonucleases (EcoRI and XhoI), and the large fragment was linked with the DNA molecule shown by SEQ ID NO: 5), to obtained a recombined plasmid. This recombined plasmid can express soluble proteins fused with 6×His tag and SMT3 domain at N-terminal.

The recombined plasmids constructed in step (1) were introduced into *Escherichia coli* BL21(DE3), to obtain recombinant *Escherichia coli* containing recombinant plasmids.

The recombinant *Escherichia coli* obtained in step (2) were inoculated in 2×YT medium (16 g peptone, 10 g yeast extract and 4 g sodium chloride were dissolved in 1000 mL distilled water), and cultured at 37° C., and when the $OD_{600}$ of the cultured bacterial liquid of the recombinant *Escherichia coli* reached 0.6 (this cultured bacterial liquid was named as pre-induced bacterial liquid), isopropyl β-D-1-thiogalactopyranoside (IPTG) was added and allowed to have a concentration of 0.4 mM in system, for induction of 24 h at 16° C. (the cultured bacterial liquid induced with IPTG was named as induced bacterial liquid).

Figure 5:
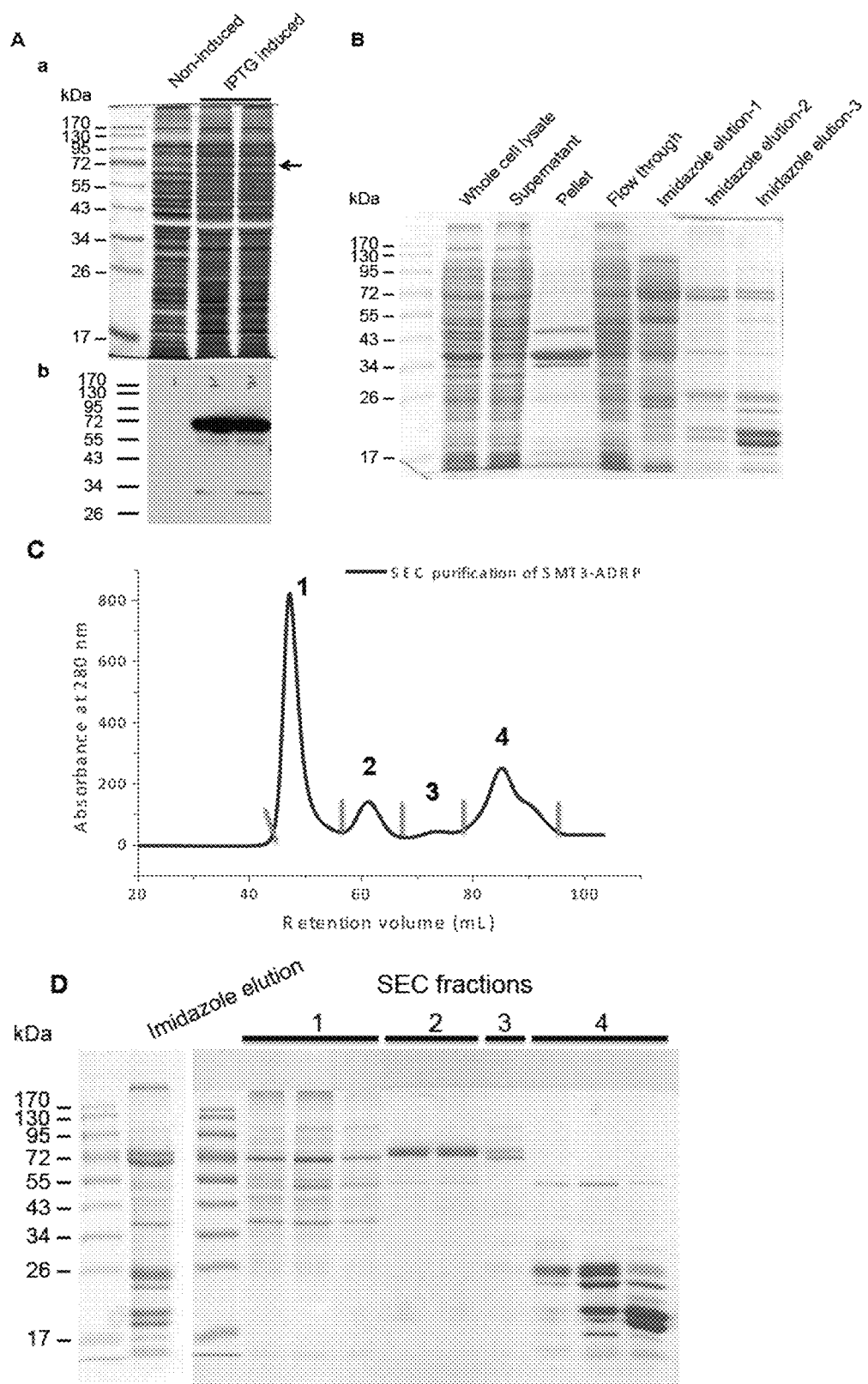

The bacteria in pre-induced bacterial liquid or induced bacterial liquid was harvested (4000 rpm, centrifugation for 20 min), respectively, and resuspended in buffer T, and then lysed with a high-pressure cell press (JNBIO JN-3000 PLUS), to obtain whole cell lysates. The whole cell lysates were subjected to SDS-PAGE, and then analyzed by silver staining and Western blot. The results showed (A in FIG. 5, in which a was the analysis result of silver staining, b was the analysis result of Western blot, arrows indicated the band to which SMT3-Perilipin-2 proteins corresponded) that SMT3-Perilipin-2 proteins in induced bacterial liquid were expressed in large quantities.

(4) The whole cell lysates of bacteria in induced bacterial liquid of step (3) were taken to centrifuge at 30000 g for 50 min, to obtain supernatant and precipitate. The supernatant was loaded into nickel ion metal affinity chromatography column (the filler was Chelating Sepharose Fast Flow chelated with nickel ions, the column was purchased from Thermo Fischer, with the product item: 29924, column volume: 4 mL, inner diameter: 1.2 cm), and eluted firstly with buffer T containing 20 mM imidazole for 12 column volumes to remove non-target protein once, and then eluted with buffer T containing 500 mM imidazole for 3 column volumes to harvest target proteins (all buffer T passing the column contained target proteins) twice. Then, buffer exchange was carried out to remove imidazole using centrifugal ultrafiltration tube (the product of Amicon Millipore-Sigma) and repurified with Size Exclusive Chromatography (SEC) (HiLoad 16/600 Superdex 200 column, the product of GE Healthcare), eluting rate: 0.8 mL/min. According to retention volume, four fractions were harvested, and named as fraction 1 (retention volume: 45 mL-57 mL), fraction 2 (retention volume: 57 mL-67 mL), fraction 3 (retention volume: 67 mL-79 mL) and fraction 4 (retention volume: 79 mL-94 mL), respectively.

The various fractions purified by the nickel ion metal affinity chromatography column were subjected to SDS-PAGE and then were stained with colloidal blue. The results were shown in B in FIG. 5 (lanes are whole cell lysate, supernatant, precipitate, flow-through, imidazole eluent-1

(20 mM imidazole eluent), imidazole eluent-2 (first partion of 500 mM imidazole eluent), and imidazole eluent-3 (second partion of 500 mM imidazole eluent) in turn. The results of Size Exclusive Chromatography molecule sieve purification were shown in C of FIG. 5 (peak 1 for fraction 1, peak 2 for fraction 2, peak 3 for fraction 3, and peak 4 for fraction 4). Both 500 mM imidazole eluents (i.e., the combination of imidazole eluent-2 and imidazole eluent-3) (left graph of D in FIG. 5) and four fractions purified by Size Exclusive Chromatography (fraction 1, fraction 2, fraction 3 and fraction 4) (right graph of D in FIG. 5) were subjected to SDS-PAGE and colloidal blue staining. The results showed that fraction 1 contained purified SMT3-Perilipin-2 proteins.

2, Expression and Purification of MLDS Proteins

According to the above method, the DNA molecule shown by SEQ ID NO: 5 in Sequence Listing of the (1) of step 1 was replaced with the DNA molecule shown by SEQ ID NO: 1 in Sequence Listing, vector pET28a-SMT3 was replaced with vector pGEX-6p-1, restriction enzyme XhoI was replaced with BamHI, and nickel ion metal affinity chromatography column in the (4) of step 1 was replaced with GST affinity chromatography column, and imidazole was replaced with reduced glutathione, without other changes in other steps, and thus purified MLDS proteins were obtained.

3, Expression and Purification of MDT-28 Proteins

According to the above method, the DNA molecule shown by SEQ ID NO: 5 in Sequence Listing of the (1) of step 1 was replaced with the DNA molecule shown by SEQ ID NO: 3 in Sequence Listing, vector pET28a-SMT3 was replaced with vector pGEX-6p-1, restriction enzyme EcoRI and XhoI were replaced with restriction enzyme BamHI and NotI, and nickel ion metal affinity chromatography column in the (4) of step 1 was replaced with GST affinity chromatography column, and imidazole was replaced with reduced glutathione, without other changes in other steps, and thus purified MDT-28 proteins were obtained.

4, Expression and Purification of MLDS-GFP Fusion Proteins

According to the above method, the DNA molecule shown by SEQ ID NO: 5 in Sequence Listing of the (1) of step 1 was replaced with the DNA molecule shown by SEQ ID NO: 9 in Sequence Listing, and vector pET28a-SMT3 was replaced with vector pET28a, without other changes in other steps, and thus purified MLDS-GFP fusion proteins were obtained.

5, Expression and Purification of MDT-28-GFP Fusion Proteins

According to the above method, the DNA molecule shown by SEQ ID NO: 5 in Sequence Listing of the (1) of step 1 was replaced with the DNA molecule shown by SEQ ID NO: 11 in Sequence Listing, vector pET28a-SMT3 was replaced with vector pET28a, and restriction enzyme EcoRI was replaced with restriction enzyme BamHI, without other changes in other steps, and thus purified MDT-28-GFP fusion proteins were obtained.

6, Expression and Purification of Perilipin-2-GFP Fusion Proteins

According to the above method, the DNA molecule shown by SEQ ID NO: 5 in Sequence Listing of the (1) of step 1 was replaced with the DNA molecule shown by SEQ ID NO: 13 in Sequence Listing, and vector pET28a-SMT3 was replaced with vector pET28a, without other changes in other steps, and thus purified Perilipin-2-GFP fusion proteins were obtained.

7, Expression and Purification of SMT3-ATGL Proteins

According to the above method, the DNA molecule shown by SEQ ID NO: 5 in Sequence Listing of the (1) of step 1 was replaced with the DNA molecule shown by SEQ ID NO: 7 in Sequence Listing, and *Escherichia coli* BL21 (DE3) in the (2) of step 1 was replaced with *Escherichia coli* Rosetta, without other changes in other steps, and thus purified SMT3-ATGL proteins were obtained.

8, Expression and Purification of Apo A-I

According to the method recorded in Peitsch, M. C. et al., A purification method for apolipoprotein A-I and A-II. Anal Biochem 178, 301-305 (1989), the content of which hereby incorporated by reference in its entirety, the purified Apo A-I was obtained.

II, Recruitment of Resident Proteins and/or Functional Proteins and/or Apolipoprotein to Adiposomes 1, Recruitment and Distribution of Resident Proteins Recruitment of Perilipin-2 Proteins a1, 5 µg SMT3-Perilipin-2 proteins, 25 ng Ulp1 and 500 adiposome a prepared in Example 1 were mixed to obtain 1000 mixed system.

a2, After the step a1 was completed, a mixed system was obtained by incubating at room temperature for 1 h (the practical operation may be performed on ice).

a3, After the step a2 was completed, the mixed system was taken to centrifuge at 20000 g for 5 min, and the liquid phase system presented two layers (the upper layer was adiposomes). The lower solution was drawn out and the upper layer was kept.

a4, The upper layer after the step a3 was resuspended into 1000 buffer B and centrifuged at 20000 g for 5 min, and the liquid phase system presented two layers (the upper layer was adiposomes). The lower solution was drawn out and the upper layer was kept.

a5, The upper layer after the step a4 was resuspended into 1000 buffer B and centrifuged at 20000 g for 5 min, and the liquid phase system presented two layers. The lower solution was drawn out and the upper layer was kept (i.e., adiposomes).

5 µg SMT3-Perilipin-2 proteins, adiposomes obtained in the step a5 and the lower solution drawn in the step a3 were all subjected to SDS-PAGE, followed by silver staining detection.

Figure 6:
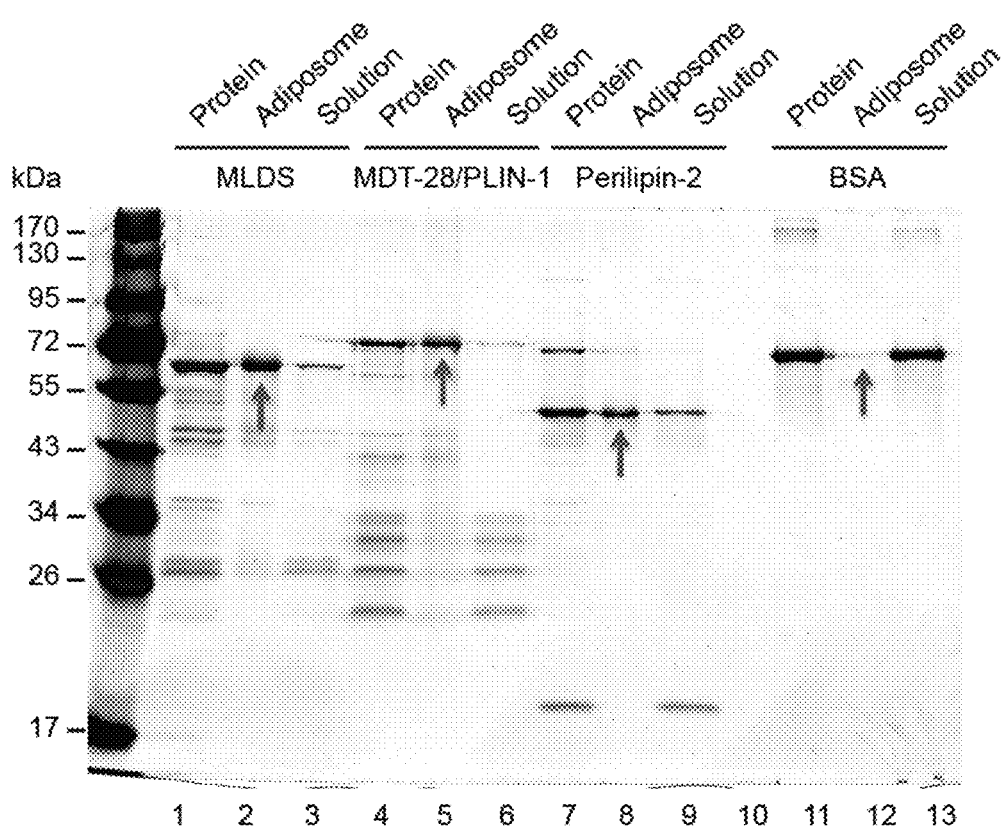

The results were seen from lanes 7, 8 and 9 in FIG. 6 (lane 7 was total proteins (SMT3-Perilipin-2 proteins), lane 8 was adiposome recruited proteins (adiposomes obtained in the step a5), and lane 9 was solution proteins (the lower solution drawn in the step a3)). The results showed that, about 50% of Perilipin-2 proteins were recruited to adiposome a. The adiposomes recruited with Perilipin-2 proteins were named as artificial lipid droplet Perilipin-2.

Figure 7:
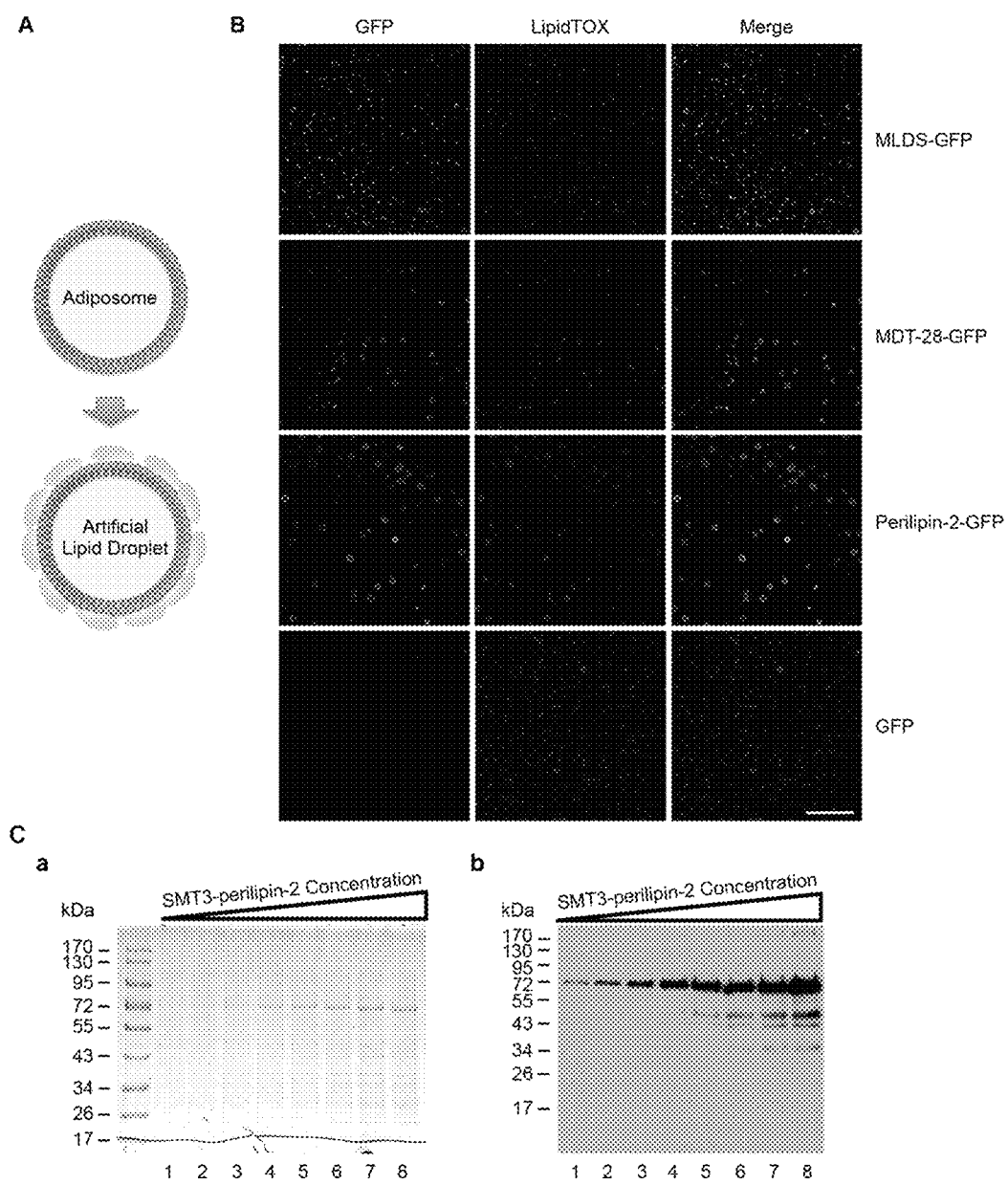

Determination of protein saturation degree: SMT3-Perilipin-2 proteins, 25 ng Ulp1 and 30 µl adiposome a prepared in Example 1 were mixed to obtain 50 µl mixed system, and the concentrations of SMT3-Perilipin-2 proteins in the mixed system were 0.015 µg/µl, 0.030 µg/µl, 0.056 µg/µl, 0.080 µg/µl, 0.101 µg/µl, 0.137 µg/µl, 0.166 µg/µl or 0.191 µg/µl. Then, artificial lipid droplets were obtained according to the above steps a2 to a5, and were subjected to SDS-PAGE, followed by staining with colloid blue, or were subjected to Western blot detection using Perilipin-2 antibody as primary antibody. The results were seen from C in FIG. 7 (in which a was the result of colloid blue staining, b was the result of Western blot detection). The results showed that the recruitment of Perilipin-2 proteins on adiposomes was saturable.

(2) The Recruitment of MLDS Proteins b1, 5 μg MLDS proteins and 50 μl adiposome a prepared in Example 1 were mixed to obtain 1000 mixed system.

b2, After the step b1 was completed, a mixed system was obtained by incubating at room temperature for 1 h (the practical operation may be performed on ice).

b3, After the step b2 was completed, the mixed system was taken to centrifuge at 20000 g for 5 min, and the liquid phase system presented two layers (the upper layer was adiposomes). The lower solution was drawn out and the upper layer was kept.

b4, The upper layer after the step b3 was resuspended into 1000 buffer B and centrifuged at 20000 g for 5 min, and the liquid phase system presented two layers (the upper layer was adiposomes). The lower solution was drawn out and the upper layer was kept.

b5, The upper layer after the step b4 was resuspended into 1000 buffer B and centrifuged at 20000 g for 5 min, and the liquid phase system presented two layers. The lower solution was drawn out and the upper layer was kept (i.e., adiposomes).

5 μg MLDS proteins, adiposomes obtained in the step b5 and the lower solution drawn in the step b3 were all subjected to SDS-PAGE, followed by silver staining detection.

The results were seen from lanes 1, 2 and 3 in FIG. 6 (lane 1 was total proteins (MLDS proteins), lane 2 was adiposome recruited proteins (adiposomes obtained in the step b5), and lane 3 was solution proteins (the lower solution drawn in the step b3)). The results showed that about 80% of MLDS proteins were recruited to adiposome a. The adiposomes recruited with MLDS proteins were named as artificial lipid droplet MLDS.

(3) The Recruitment of MDT-28 Proteins

The MLDS proteins in the step (2) were replaced with MDT-28 proteins, without other changes in other steps. The results were seen from lanes 4, 5 and 6 in FIG. 6 (lane 4 was total proteins (MDT-28 proteins), lane 5 was adiposome recruited proteins, and lane 6 was solution proteins). The results showed that about 90% of MDT-28 proteins were recruited to adiposome a. The adiposomes recruited with MDT-28 proteins were named as artificial lipid droplet MDT-28.

(4) The Recruitment of Bovine Serum Albumin

The MLDS proteins in the step (2) were replaced with Bovine serum albumin, without other changes in other steps. The results were seen from lanes 11, 12 and 13 in FIG. 6 (lane 11 was total proteins (Bovine serum albumin), lane 12 was adiposome recruited proteins, and lane 13 was solution proteins). The results showed that no Bovine serum albumin was recruited to adiposome a.

The adiposomes recruited with proteins were named as artificial lipid droplets.

(5) The Distribution of Resident Proteins on Artificial Lipid Droplets

5 μg SMT3-Perilipin-2 proteins were replaced with 10 μg purified Perilipin-2-GFP fusion proteins, without other changes in other steps, to obtained artificial lipid droplet Perilipin-2-GFP. 5 μg MLDS proteins in the (2) of step 1 were replaced with 10 μg purified MLDS-GFP fusion proteins, to obtain artificial lipid droplet MLDS-GFP. 5 μg MDT-28 proteins in the (3) of step 1 were replaced with 10 μg MDT-28-GFP fusion proteins, to obtain artificial lipid droplet MDT-28-GFP.

Figure 8:
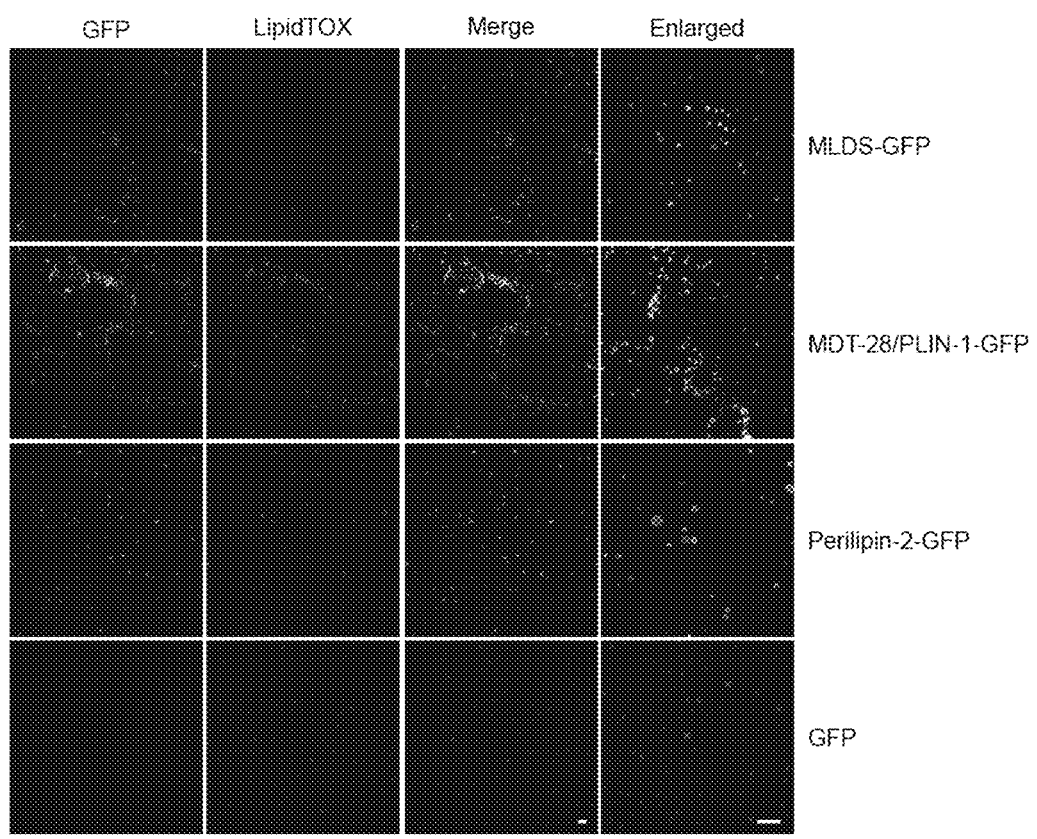
FIG. 8 is that adiposomes recruit lipid droplet resident/structural proteins-GFP fusion proteins (scale=5 μm).

Then, artificial lipid droplets were observed under confocal microscope. The results showed (B in FIG. 7 and FIG. 8) that the fluorescence proteins on artificial lipid droplets presented circle structure, and Perilipin-2-GFP fusion proteins, MLDS-GFP fusion proteins and MDT-28-GFP fusion proteins all were uniformly distributed on the surface of artificial lipid droplets, occasionally large aggregates of fluorescent proteins can be observed, without detection of free GFP; artificial lipid droplets were observed using OMX DeltaVision (SIM) super-resolution microscope, and the proteins on artificial lipid droplets still represented a state of uniform distribution.

2, The Recruitment of Functional Proteins ATG

SMT3-Perilipin-2 proteins in the (1) of step 1 were replaced with SMT3-ATGL proteins, and 50 μl adiposome a was replaced with 30 μl adiposome a, without other changes in other steps, to obtain adiposomes recruited with ATGL.

Figure 9:
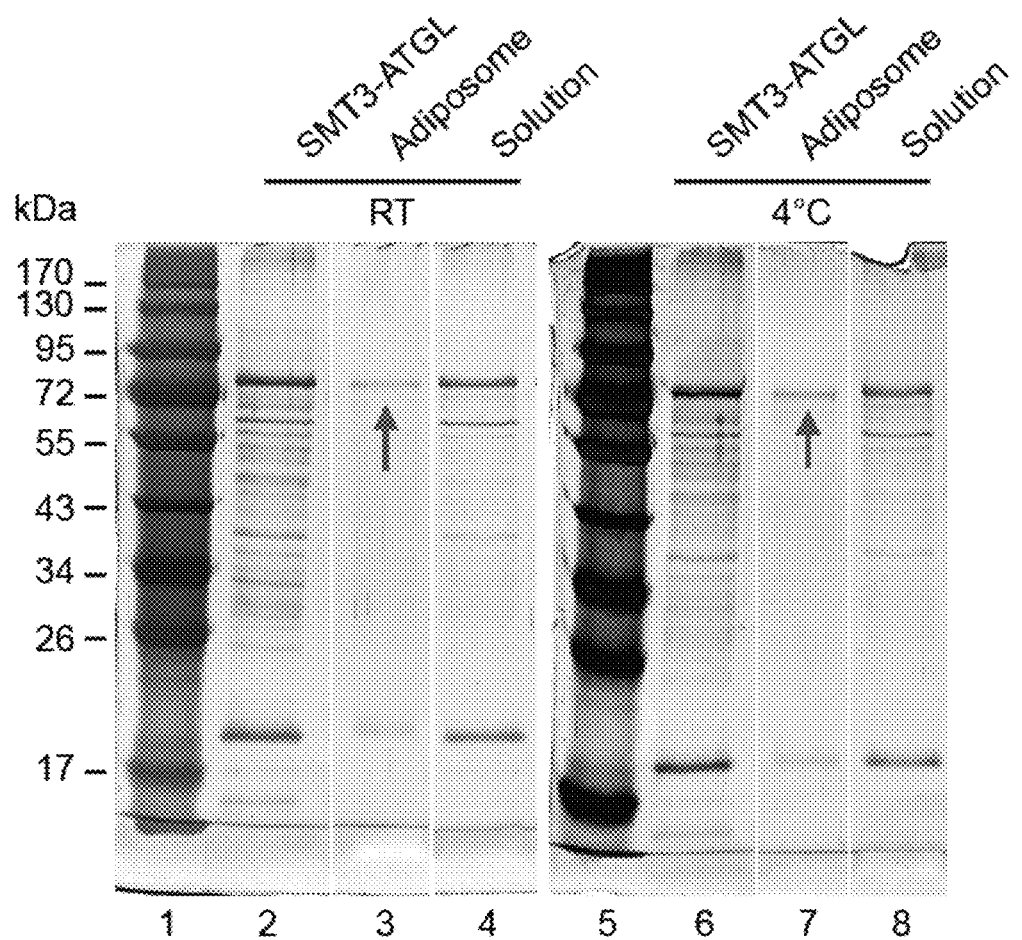
FIG. 9 is the silver staining analysis result of SMT3-ATGL proteins incubated with adiposomes at room-temperature or 4° C.

The results were seen from FIG. 9 (the left graph was the experiment result of incubating at normal temperature, and the right graph was the experiment result of incubating at 4° C., in which lanes 1 and 5 were Marker, lanes 2 and 6 were total proteins (SMT3-ATGL proteins), lanes 3 and 7 were adiposome recruited proteins, and lanes 4 and 8 were solution proteins). The results showed that, about ⅓ of ATGL was recruited to adiposome a. The adiposome recruited with ATGL was named as artificial lipid droplet ATGL.

Determination of protein saturation degree: SMT3-ATGL proteins, and 500 adiposome a prepared in Example 1 were mixed to obtain 1000 mixed system, and the concentrations of SMT3-ATGL proteins in the mixed system were 0.091 μg/μl, 0.132 μg/μl, 0.171 μg/μl, 0.209 μg/μl, 0.244 μg/μl, 0.278 μg/μl or 0.310 μg/μl. Then artificial lipid droplets were obtained according to the a2 to a5 of step 1, and were subjected to SDS-PAGE, followed by silver staining, or were subjected to Western blot detection using ATGL antibody (Cell Signaling Technology, Danvers, Mass., the product item: 2138) as primary antibody. The results were seen from A in FIG. 10 (in which a was the result of silver staining, and b was the result of Western blot detection). The results showed that when the concentration of ATGL in the reaction system was 0.209 μg/μl, the recruitment of ATGL on adiposomes reached saturation.

3, The Recruitment of Apolipoproteins

5 μg MLDS proteins in the (2) of step 1 were replaced with 9 μg Apo A-I, without other changes in other steps, to obtain adiposomes recruited with Apo A-I. The results were seen from B in FIG. 10 (lane 1 was adiposome recruited proteins, lane 2 was solution proteins, and lane 3 was total proteins (Apo A-I)). The results showed that about 50% of Apo A-I was recruited to adiposome a. The adiposome recruited with Apo A-I was named as artificial lipoprotein Apo A-I.

Preparation of adiposome a': the method was substantially same as step I of Example 1, and the difference only lies in: commercially available glyceryl trioleate was used to replace triacylglycerol in Example 1 to obtain adiposome a' in step (5). Adiposome a' was subjected to various experiments in Example 2, and the results were substantially same as those of adiposome a, without significant difference.

Commercially available glyceryl trioleate was triolein (TO), purchased from Sigma, the product item: 92860.

Example 3, Use of Adiposomes as Drug Carriers

The drug of this Example was compounds shown as formula a;

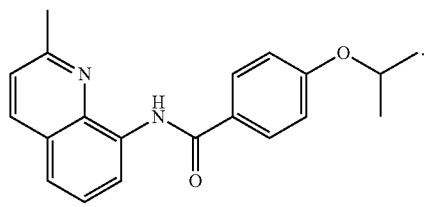

formula a

The drug was a fat-soluble drug, which is intersoluble with triolein and was a drug candidate which can treat Type II diabetes and/or metabolic disorders. The drug was particularly the product of item: 5869 of TOCRIS Bioscience, with trade name of CDN 1163. ZORBAX SB-C18 chromatographic column was the product of Agilent (Santa Clara, Calif.).

I, the Preparation of Drug-Loaded Adiposomes

1, Drug-loaded adiposomes were prepared with vortexing and two-step centrifugation, and the specific steps were as follows:

(1) 10 mg TAG was taken into a micro-centrifugal tube and 100 μl of chloroform was added for sufficient dissolution to obtain a TAG solution.

(2) 2 mg CDN 1163 was taken into another micro-centrifugal tube and 200 μl of chloroform was added for sufficient dissolution to obtain a drug solution with a concentration of 10 μg/μl.

(3) After the steps (1) and (2) were completed, the TAG solution and the drug solution were uniformly mixed, and the solvent was blow dried with highly pure nitrogen, to obtain a mixed substance (the mixed substance contained 10 mg TAG and 2 mg CDN1163).

(4) 80 μL DOPC solution (containing 2 mg DOPC therein) was taken into a new micro-centrifugal tube, and the solvent was blow dried with highly pure nitrogen.

(5) 100 μL buffer B and 6 mg mixed substance obtained in the step (3) were added into the micro-centrifugal tube in which the step (4) has been completed, vortexing for 4 min (vortexing 10 s, pausing 10 s), to obtain a milky lipid mixture A, and then the milky lipid mixture A was centrifuged at 20000 g for 5 min (centrifuging at 18000-22000 g for 3-7 min is feasible in practical use). After centrifuged, the precipitate fraction A was at the bottom of the micro-centrifugal tube, and the liquid phase system presented two layers (the upper layer was white band A, and the portion below the white band A was solution A).

(6) After the step (5) was completed, the solution A and the precipitate fraction A were removed by the means of drawing, and the white band A was kept, adding 100 μl buffer B, vortexing, to obtain a milky lipid mixture B, and the lipid mixture B was centrifuged at 20000 g for 5 min (centrifuging at 18000-22000 g for 3-7 min is feasible in practical use). After centrifuging, if there were precipitates at the bottom of the micro-centrifugal tube, the precipitates were the precipitate fraction B, and the liquid phase system presented two layers (the upper layer was white band B, and the portion below the white band B was solution B).

(7) After the step (6) was completed, the solution B and the precipitate fraction B were removed by the means of drawing, and the white band B was kept, adding 100 μl buffer B, vortexing, to obtain a milky lipid mixture C, and the lipid mixture C was centrifuged at 20000 g for 5 min (centrifuging at 18000-22000 g for 3-7 min is feasible in practical use). After centrifuged, the liquid phase system presented two layers (the upper layer was white band C, and the portion below the white band C was solution C).

The step (7) was the repeat of the step (6), and in the practical use, the number of repeating the step (6) was controlled based on that there was no precipitate in the layer under the white band.

(8) After the step (7) was completed, the white band C was taken and added with 100 μl buffer B, for uniformly vortexing, and centrifuged at 1000 g for 5 min (centrifuging at 800-1200 for 3-7 min is feasible in practical use). After centrifuged, the liquid phase system presented two layers (the upper layer was white band D, and the portion below the white band D was solution D). The solution D was collected, which is the drug-loaded adiposomes.

The specific flow of preparing drug-loaded adiposomes using the above process referred to A in FIG. 11 (in which a was the components for preparing drug-loaded adiposomes, and b was the flowchart of preparing drug-loaded adiposomes). The drug-loaded adiposomes prepared using the above process referred to B in FIG. 11 (the left was adiposome a prepared in (1) of step I of Example 1, and the right was drug-loaded adiposomes).

II, the Characteristics of Drug-Loaded Adiposomes

1, The average size of adiposome a was about 166.1 nm, as measured using dynamic light scatter (C in FIG. 11).

2, The determination of the concentration of CDN1163 in drug-loaded adiposomes. The specific steps were as follows:

(1) Drawing of Standard Curve 10 mg of CDN 1163 was accurately weighed into a 100 ml volumetric flask, dissolved and balanced to 100 ml with anhydrous methanol (chromatographic grade), to prepare 100 μg/ml CDN 1163 stock solution. Then standard solutions with concentrations of 20 μg/mL and 4 μg/mL were obtained, respectively, by continuing to dilute with anhydrous methanol (chromatographic grade). Agilent 1260 liquid chromatograph equipped with a ZORBAX SB-C18 chromatography column (5.0 μm, 4.6 mm×150 mm) was used to determine the peak area of CDN 1163 at different concentrations, 3 replicates. The mobile phase consisted of methanol and water, the volume ratio of methanol to water was 85:15, and the flow rate was 1.0 mL/min. The detection wavelength was 245 nm.

With the concentrations of CDN1163 as the X-axis and the peak areas as the Y-axis, a standard curve was plotted. The linear equation of the standard curve was: $y=61.796x+18.2$ ($R^2=0.99999$), in which y was the peak area, x was the concentration of CDN 1163 (μg/mL). The linear relationship of CDN 1163 concentration was good in 0-100 μg/ml.

(2) The determination of the concentration of CDN1163 in drug-loaded adiposomes. 10 μl drug-loaded adiposomes were taken and added with 9900 anhydrous methanol (chromatographic grade), vortexing 10 s (the purpose was to sufficiently mix), and then were centrifuged at 20000 g for 5 minutes, followed by removing precipitates and collecting supernatant. Agilent 1260 liquid chromatograph equipped with a ZORBAX SB-C18 chromatography column (5.0 μm, 4.6 mm×150 mm) was used to determine the peak area of supernatant, 3 replicates. The mobile phase consisted of methanol and water, the volume ratio of methanol to water was 85:15, and the flow rate was 1.0 mL/min. The detection wavelength was 245 nm.

The experimental results were shown in D of FIG. 11 (retention time was 6.366 min). According to the peak area of the supernatant and the standard curve of step (1), the concentration of CDN1163 in the supernatant was calculated to be 9.604 µg/ml, the concentration of CDN 1163 in drug-loaded adiposomes was further obtained as 960.4 µg/ml.

The above results showed that the adiposomes prepared in Example 1 can be used as drug carriers.

INDUSTRIAL APPLICATIONS

The adiposomes, artificial lipid droplets and artificial lipoproteins prepared by the method disclosed by the present invention can be used as drug carriers, thereby to complete various biological and medical goals, having an important application value.

The invention claimed is:

1. A method for preparing adiposomes consisting of neutral lipids and a monolayer phospholipid membrane, the method comprising:
   a1) vortexing phospholipid and neutral lipids in a buffer to enable a reaction between both, performing centrifugation, and collecting an upper liquid phase;
   wherein the adiposomes are obtained by isolation of the upper liquid phase comprising:
   a2) performing purification on the upper liquid phase obtained in step a1) twice or more, wherein each purification comprises uniformly mixing the upper liquid phase with the buffer, layering the mixture, performing centrifugation, wherein the parameters of the centrifugation are: 18000-22000 g, for 3-7 min, and collecting an upper liquid phase; and
   a3) mixing the upper liquid phase obtained in step a2) with the buffer, layering the mixture, performing centrifugation, wherein the parameters of the centrifugation are: 800-1200 g, for 3-7 min, and collecting a lower liquid phase containing adiposomes, wherein the phospholipid is b1), b2) or b3), wherein:
   b1) is 1,2-di-(9Z-octadecenoyl)-sn-glycero-3-phosphocholine;
   b2) is 1,2-di-(9Z-octadecenoyl)-sn-glycero-3-phosphocholine and 1,2-di-(9Z-octadecenoyl)-sn-glycero-3-phosphoethanolamine; and
   b3) is 1,2-di-(9Z-octadecenoyl)-sn-glycero-3-phosphocholine and 1,2-di-octadecanoyl-sn-glycero-3-phosphocholine;
      wherein, in the b2), a mass ratio of 1,2-di-(9Z-octadecenoyl)-sn-glycero-3-phosphocholine and 1,2-di-(9Zoctadecenoyl)-sn-glycero-3-phosphoethanolamine is 1:0.01-2;
      wherein, in the b3), a mass ratio of 1,2-di-(9Z-octadecenoyl)-sn-glycero-3-phosphocholine and 1,2-di-octadecanoyl-sn-glycero-3-phosphocholine is 1:0.01-2;
   wherein the neutral lipid is c1) or c2), wherein:
   c1) is triacylglycerol; and
   c2) is triacylglycerol and cholesteryl oleate,
      wherein in the c2), a mass ratio of triacylglycerol and cholesterol oleate is 1-5:1; and
   d1) wherein the mass ratio of the phospholipid and the neutral lipid is 0.25-3:5.

2. The method according to claim 1, wherein the phospholipids and neutral lipids are vortexed for 3-5 min; and in the step a1), the parameters of the centrifugation are: 18000-22000 g, for 3-7 min.

3. The method according to claim 2, wherein the phospholipids and neutral lipids are vortexed for 4 min; and wherein the parameters of the centrifugation are: 20000 g, for 5 min.

4. The method according to claim 1, wherein in the step a2), the parameters of the centrifugation are: 20000 g, for 5 min; and/or in the step a3), the parameters of the centrifugation are: 1000 g, for 5 min.

5. The method according to claim 1, wherein
   in the b2), the mass ratio of 1,2-di-(9Z-octadecenoyl)-sn-glycero-3-phosphocholine and 1,2-di-(9Z-octadecenoyl)-sn-glycero-3-phosphoethanolamine is 2:1, 1:1 or 1:2;
   in the b3), the mass ratio of 1,2-di-(9Z-octadecenoyl)-sn-glycero-3-phosphocholine and 1,2-di-octadecanoyl-sn-glycero-3-phosphocholine is 2:1, 1:1 or 1:2; and
   in the c2), the mass ratio of triacylglycerol and cholesterol oleate is 5:1, 4:1, 3:1 or 2:1.

6. The method according to claim 1, wherein the mass ratio of the phospholipid and the neutral lipid is any one of d2) to d6), wherein: d2) is 3:5; d3) is 2:5; d4) is 1:5; d5) is 1:10; and d6) is 1:20.

7. Adiposomes prepared by the method according to claim 1.

8. A method for preparing artificial lipid droplets, comprising recruiting one or more resident proteins and/or functional proteins to the adiposomes prepared by the method according to claim 1 to obtain the artificial lipid droplets.

9. The method according to claim 8, wherein the resident proteins are MLDS proteins, MDT-28 proteins or Perilipin-2 proteins; and the functional proteins are ATGL; wherein
   the MLDS proteins are e1) or e2), wherein
      e1) proteins comprise SEQ ID NO: 2 in the Sequence Listing;
      e2) proteins comprise one to ten amino acid residue substitutions, deletions, or additions to the proteins shown in e1);
   the MDT-28 proteins are f1) or f2), wherein
      f1) proteins comprise SEQ ID NO: 4 in the Sequence Listing;
      f2) proteins comprise one to ten amino acid residue substitutions, deletions, or additions to the proteins shown in f1);
   the Perilipin-2 proteins are g1) or g2), wherein
      g1) proteins comprise SEQ ID NO: 6 in the Sequence Listing;
      g2) proteins comprise one to ten amino acid residue substitutions, deletions, or additions to the proteins shown in g1); and
   the ATGL are h1) or h2), wherein
      h1) proteins comprise SEQ ID NO: 8 in the Sequence Listing;
      h2) proteins comprise one to ten amino acid residue substitutions, deletions, or additions to the proteins shown in h1).

10. Artificial lipid droplets prepared by the method according to claim 8.

11. A method of preparing artificial lipoproteins, comprising recruiting one or more apolipoproteins to the adiposomes according to claim 7, to obtain the artificial lipoproteins.

12. The method according to claim 11, wherein the apolipoprotein is Apo A-I.

13. Artificial lipoproteins prepared by the method according to claim 11.

14. A drug carrier, the active components of which are adiposomes loaded with medicinal compounds; and the adiposomes are the adiposomes according to claim 7.

15. The drug carrier according to claim 14, wherein the medicinal compound is a fat-soluble drug.

16. The drug carrier according to claim 14, wherein the medicinal compound is a drug or a drug candidate which can treat Type II diabetes and/or metabolic disorders.

* * * * *